US008796653B2

(12) United States Patent
Schulkin et al.

(10) Patent No.: US 8,796,653 B2
(45) Date of Patent: Aug. 5, 2014

(54) TERAHERTZ RADIATION SOURCE MOUNTING ARRANGEMENTS AND METHODS OF MOUNTING A TERAHERTZ SOURCE

(75) Inventors: Brian Schulkin, Troy, NY (US);
Xi-Cheng Zhang, Troy, NY (US);
Thomas Tongue, Niskayuna, NY (US);
Jingzhou Xu, Ann Arbor, MI (US); Jian Chen, Troy, MI (US)

(73) Assignee: Rensselaer Polytechnic Institute, Troy, NY (US)

( * ) Notice: Subject to any disclaimer, the term of this patent is extended or adjusted under 35 U.S.C. 154(b) by 989 days.

(21) Appl. No.: 12/886,131

(22) Filed: Sep. 20, 2010

(65) Prior Publication Data

US 2011/0006226 A1 Jan. 13, 2011

Related U.S. Application Data

(63) Continuation of application No. 12/013,167, filed on Jan. 11, 2008, now Pat. No. 7,808,636.

(60) Provisional application No. 60/884,443, filed on Jan. 11, 2007, provisional application No. 60/884,446, filed on Jan. 11, 2007, provisional application No. 60/884,428, filed on Jan. 11, 2007, provisional application No. 60/884,449, filed on Jan. 11, 2007.

(51) Int. Cl.
*H01J 29/02* (2006.01)
*H01S 5/022* (2006.01)

(52) U.S. Cl.
CPC ......... *H01S 5/02236* (2013.01); *H01S 2302/02* (2013.01)
USPC ..................................... 250/522.1

(58) Field of Classification Search
CPC ................. H01L 33/62; F21V 19/00; H01S 2302/00–2302/02; H01S 5/02236–5/02276
See application file for complete search history.

(56) References Cited

U.S. PATENT DOCUMENTS

| 2,126,410 A | 8/1938 | Pineo |
| 4,171,908 A | 10/1979 | Robert et al. |

(Continued)

FOREIGN PATENT DOCUMENTS

| GB | 2393260 | 9/2002 |
| JP | 2005037213 | 2/2005 |
| WO | 2006092874 | 9/2006 |

OTHER PUBLICATIONS

Planken, et al., "Measurement and Calculation of the Orientation Dependence of Terahertz Pulse Detection in ZnTe," vol. 18, No. 3, Mar. 2001, Journal of the Optical Society of America, pp. 313-317.

(Continued)

*Primary Examiner* — Gregory J Toatley
*Assistant Examiner* — Juan D Valentin, II
(74) *Attorney, Agent, or Firm* — Heslin Rothenberg Farley & Mesiti P.C.

(57) ABSTRACT

Methods and apparatus for detecting variations in electromagnetic fields, in particular, terahertz (THz) electromagnetic fields, are provided. The methods and apparatus employ polarization detection devices and controllers to maintain or vary the polarization of modulated signals as desired. The methods and apparatus are provided to characterize electromagnetic fields by directing the electromagnetic field and a probe beam upon an electro-crystal and detecting the modulation of the resulting probe beam. Detection of the modulation of the probe beam is practiced by detecting and comparing the polarization components of the modulated probe beam. Aspects of the invention may be used to analyze or detect explosives, explosive related compounds, and pharmaceuticals, among other substances. A compact apparatus, modular optical devices for use with the apparatus, sample holders, and radiation source mounts are also disclosed.

16 Claims, 25 Drawing Sheets

(56) References Cited

U.S. PATENT DOCUMENTS

| | | | |
|---|---|---|---|
| 4,410,277 A | 10/1983 | Yamamoto et al. | |
| 4,695,727 A | 9/1987 | Brierley et al. | |
| 4,727,550 A | 2/1988 | Chang et al. | |
| 5,280,177 A | 1/1994 | Bruno | |
| 5,470,757 A | 11/1995 | Gagnon et al. | |
| 5,543,960 A | 8/1996 | Carrig et al. | |
| 5,574,562 A | 11/1996 | Fishman et al. | |
| 5,623,145 A | 4/1997 | Nuss | |
| 5,663,639 A | 9/1997 | Brown et al. | |
| 5,729,017 A | 3/1998 | Brener et al. | |
| 5,764,355 A | 6/1998 | Gagnon et al. | |
| 5,789,750 A | 8/1998 | Nuss | |
| 5,914,497 A | 6/1999 | Sherwin | |
| 5,939,721 A | 8/1999 | Jacobsen et al. | |
| 5,952,818 A | 9/1999 | Zhang et al. | |
| 6,002,475 A | 12/1999 | Boyd et al. | |
| 6,055,815 A * | 5/2000 | Peterson | 62/3.7 |
| 6,111,416 A | 8/2000 | Zhang et al. | |
| 6,144,679 A | 11/2000 | Herman et al. | |
| 6,157,446 A | 12/2000 | Baer et al. | |
| 6,239,445 B1 | 5/2001 | Shaeef | |
| 6,239,866 B1 | 5/2001 | Bromage et al. | |
| 6,476,596 B1 | 11/2002 | Wraback et al. | |
| 6,479,822 B1 | 11/2002 | Nelson et al. | |
| 6,531,095 B2 | 3/2003 | Hammer et al. | |
| 6,605,808 B2 | 8/2003 | Mickan et al. | |
| 6,697,186 B2 | 2/2004 | Kawase et al. | |
| 6,723,991 B1 | 4/2004 | Sucha et al. | |
| 6,734,974 B2 | 5/2004 | Jiang et al. | |
| 6,738,397 B2 | 5/2004 | Yamamoto et al. | |
| 6,747,736 B2 | 6/2004 | Takahashi | |
| 6,813,021 B2 | 11/2004 | Chung et al. | |
| 6,816,647 B1 * | 11/2004 | Rudd et al. | 250/208.4 |
| 6,844,552 B2 | 1/2005 | Zhang et al. | |
| 6,847,448 B2 | 1/2005 | Nagashima et al. | |
| 6,849,852 B2 | 2/2005 | Williamson | |
| 6,865,014 B2 | 3/2005 | Ciesla et al. | |
| 6,909,104 B1 | 6/2005 | Koops et al. | |
| 6,958,853 B1 | 10/2005 | Arnone et al. | |
| 7,091,506 B2 | 8/2006 | Zhang et al. | |
| 7,119,339 B2 | 10/2006 | Ferguson et al. | |
| 7,122,813 B2 | 10/2006 | Linfield et al. | |
| 7,177,071 B2 | 2/2007 | Ohtake et al. | |
| 2001/0038074 A1 | 11/2001 | Zhang et al. | |
| 2001/0052981 A1 | 12/2001 | Chung et al. | |
| 2002/0061597 A1 | 5/2002 | Herpst | |
| 2002/0067480 A1 | 6/2002 | Takahashi | |
| 2002/0074500 A1 | 6/2002 | Mickan et al. | |
| 2003/0016358 A1 | 1/2003 | Nagashima et al. | |
| 2003/0165003 A1 | 9/2003 | Ciesla et al. | |
| 2004/0196660 A1 | 10/2004 | Usami | |
| 2004/0238760 A1 | 12/2004 | Linfield et al. | |
| 2004/0262499 A1 | 12/2004 | Martinelli et al. | |
| 2004/0262544 A1 | 12/2004 | Zhang et al. | |
| 2005/0036146 A1 | 2/2005 | Braig et al. | |
| 2005/0156110 A1 | 7/2005 | Crawely | |
| 2005/0174808 A1 * | 8/2005 | Butsch et al. | 362/652 |
| 2005/0179905 A1 | 8/2005 | Ohtake et al. | |
| 2005/0264815 A1 | 12/2005 | Wechsler et al. | |
| 2006/0022140 A1 | 2/2006 | Connelly et al. | |
| 2006/0056586 A1 | 3/2006 | Uetake et al. | |
| 2006/0109181 A1 | 5/2006 | Salsman | |
| 2006/0151722 A1 | 7/2006 | Cole et al. | |
| 2006/0231762 A1 | 10/2006 | Ohtake et al. | |
| 2007/0034813 A1 | 2/2007 | Shen et al. | |
| 2009/0262766 A1 * | 10/2009 | Chen et al. | 372/26 |
| 2011/0235357 A1 * | 9/2011 | Myojin et al. | 362/519 |
| 2011/0249469 A1 * | 10/2011 | Lee et al. | 362/612 |

OTHER PUBLICATIONS

Buma, et al., "Coded Excitation of Broadband Terahertz Using Optical Rectification in Poled Lithium Niobate," Applied Physics Letters 87, 251005 (2005) American Institute of Physics, pp. 251105-1-251105-3.

Welsh, et al., "Terahertz-Pulse Emission Through Laser Excitation of Surface Plasmons in a Metal Grating," Physical Review Letters 98, 026803 (2007), The American Physical Society, pp. 026803-1-026803-4.

Kübler, et al., "Ultrabroadband Detection of Multi-Terahertz Field Transients with GaSe Electro-Optic Sensors: Approaching the Near Infrared," Applied Physics Letters, vol. 85, No. 16, Oct. 18, 2004, American Institute of Physics, pp. 3360-3362.

Non-Final Office Action for U.S. Appl. No. 12/013,167 mailed Oct. 5, 2009.

International Search Report corresponding to International PCT application PCT/US 08/50926 mailed Feb. 24, 2009.

Written Opinion corresponding to International PCT application PCT/US 08/50926 mailed Feb. 24, 2009.

* cited by examiner

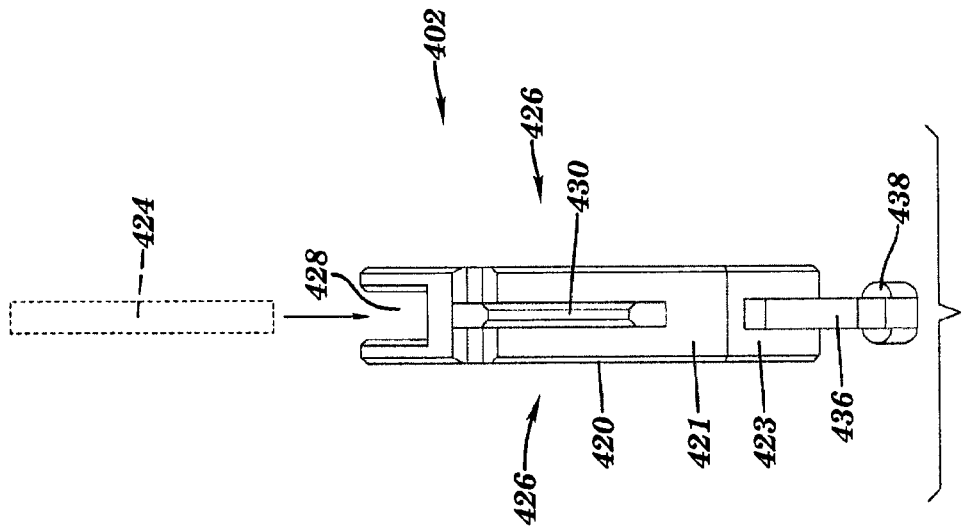
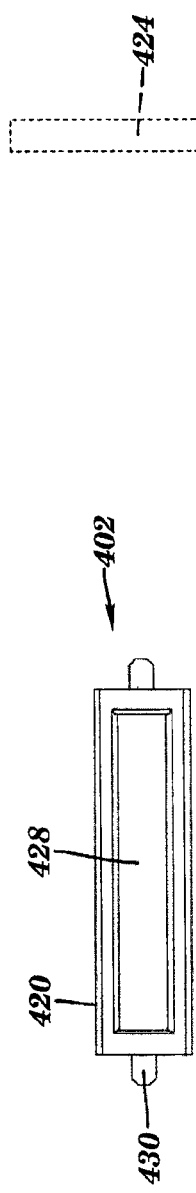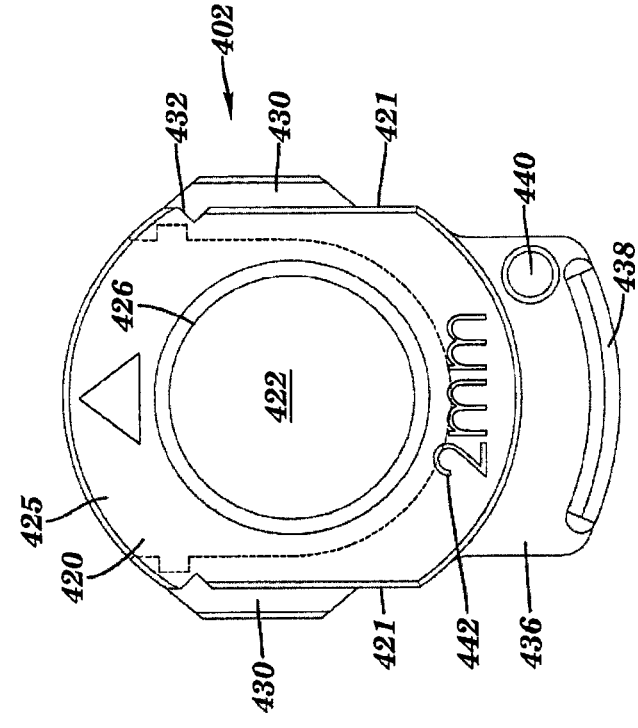

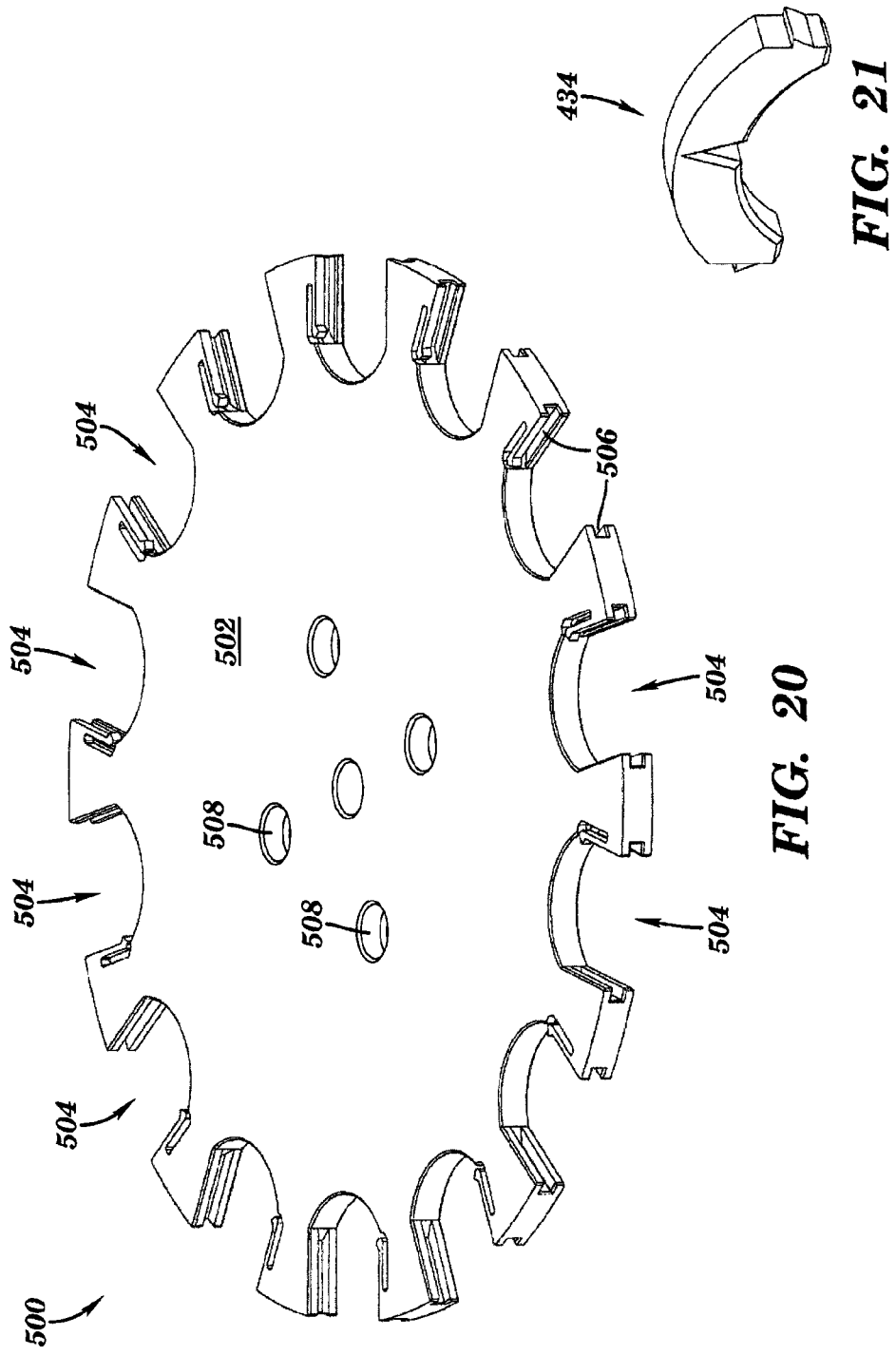

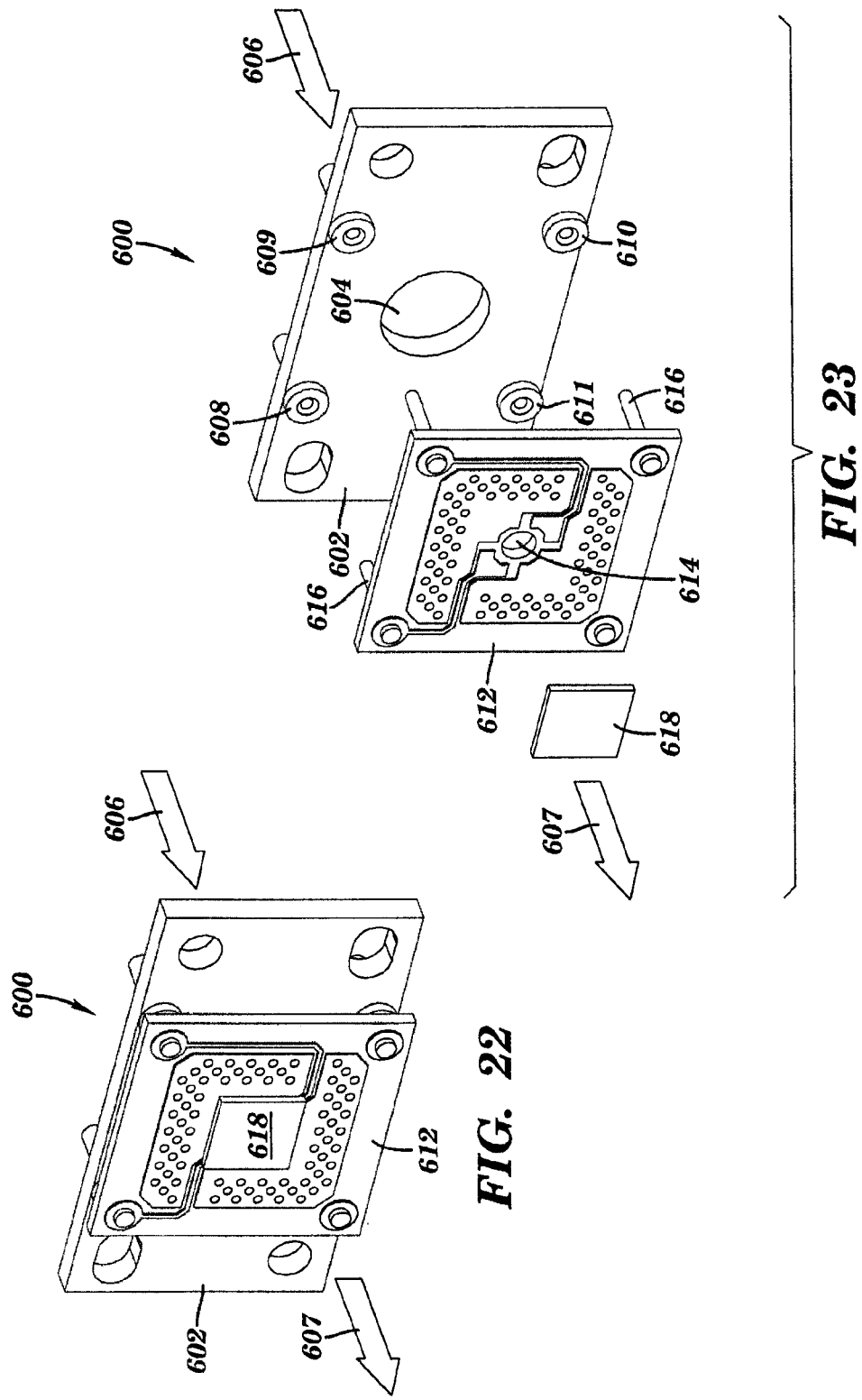

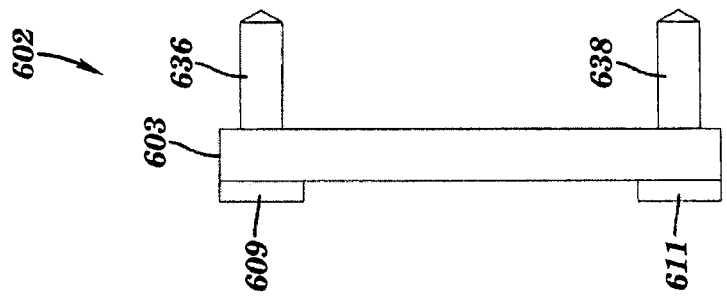
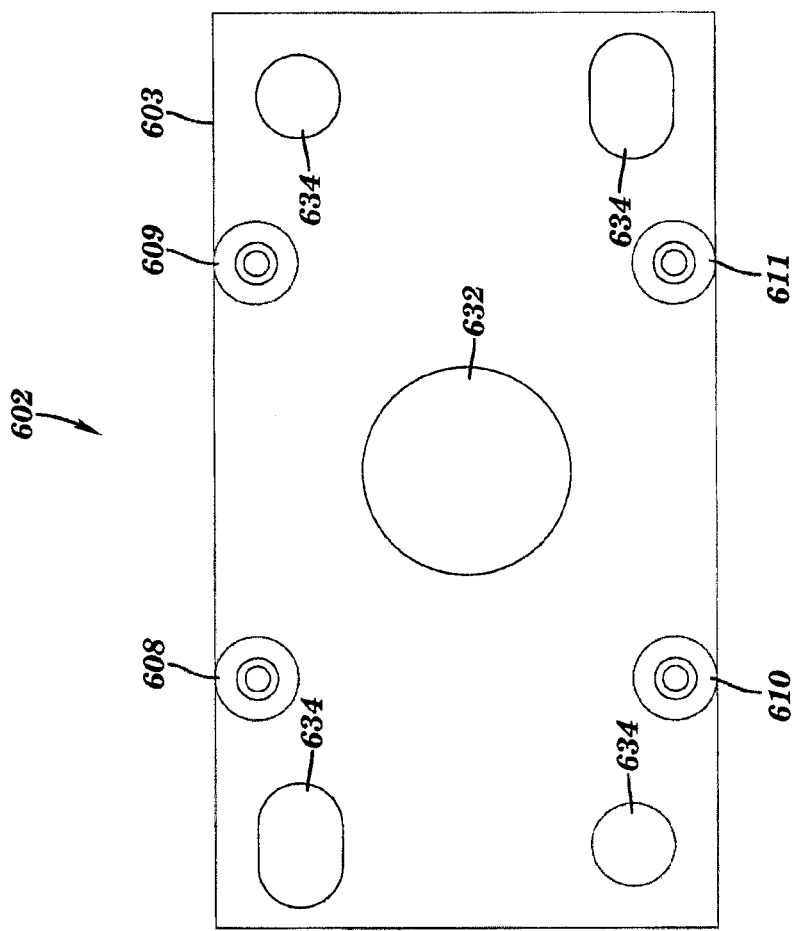
FIG. 28
FIG. 27

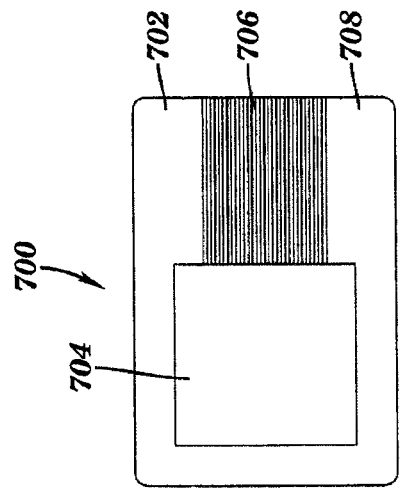
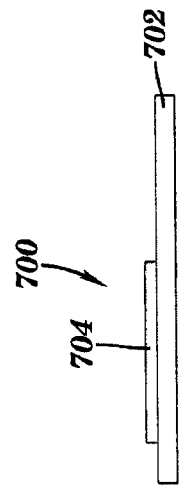
FIG. 30A
FIG. 30B
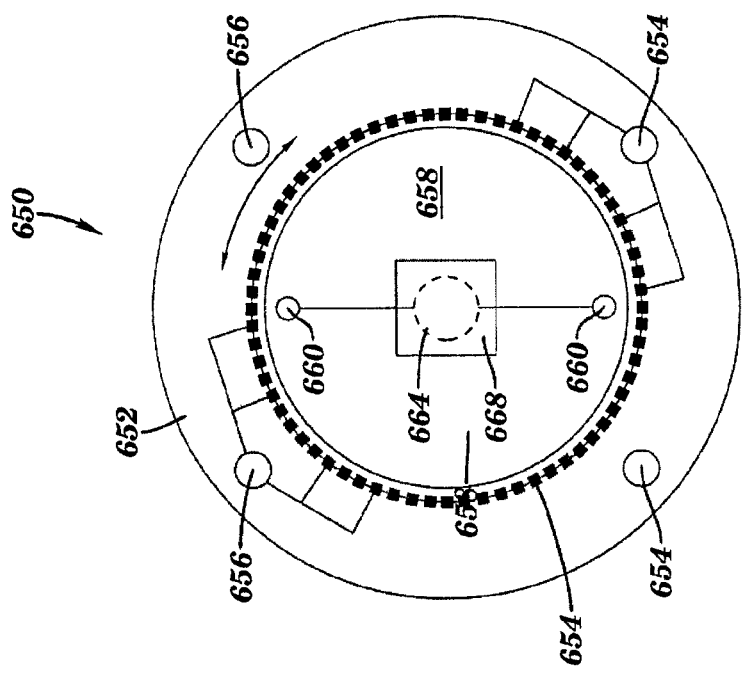
FIG. 29

TERAHERTZ RADIATION SOURCE MOUNTING ARRANGEMENTS AND METHODS OF MOUNTING A TERAHERTZ SOURCE

CROSS-REFERENCE TO RELATED APPLICATION

This application is a continuation application of pending U.S. application Ser. No. 12/013,167 filed on Jan. 11, 2008, now U.S. Pat. No. 7,808,636, which claims priority from U.S. Provisional Patent Applications 60/884,428; 60/884,443; 60/884,446; and 60/884,449, all filed on Jan. 11, 2007. The disclosures of these applications are included by reference herein in their entirety.

STATE AND FEDERAL FUNDED RESEARCH

The invention described herein was made with support of the National Science Foundation under Federal Grant Number ECS-0621522, "THz Wave Photonics." The invention described herein was also made with support of the Army Research Office under Federal Grant Number ARO-MURI through subcontract with Johns Hopkins University under grant 8202-05776, "Spectroscopic and Time-domain Detection of Trace Explosives in Condensed and Vapor Phases." The U.S. Government may have certain rights to this invention.

BACKGROUND OF THE INVENTION

1. Technical Field

The present invention relates to apparatus, methods, and devices for use in characterizing a free-space electromagnetic field, and in particular, to apparatus and methods suitable for real-time two-dimensional far-infrared imaging applications.

2. Related Art

In the ever more dangerous environment that exists in international relations that prevails in the early $21^{st}$ century, the detection of explosive devices and the explosive compounds they contain has become critical. The development of efficient explosive sensing devices with state-of-the-art science and technology is a top priority among many defense related research and development projects. Among the many techniques being pursued, the use and sensing of terahertz (THz) radiation has proven to be innovative sensing and imaging technology. The use and sensing of THz radiation can provide spectroscopic information of most explosives and their related compounds, promising for the standoff detection and identification of explosive, and non-explosive, targets.

THz technology is well accepted by both industry and government for use for non-destructive evaluation (NDE), imaging, and sensing of materials which exhibit spectral fingerprints in the THz frequency range. Most materials which exhibit such fingerprints are drugs, explosives and related compounds, and other hazardous materials. For example, more than 14 explosives and their explosive related compounds (ERCs) have been measured by using THz wave time-domain spectroscopy, their spectroscopic signatures in THz frequency range have been reported in the literature.

However, typical prior art THz systems have very limited portability and mobility due to the large size of, for example, their Ti:sapphire lasers commonly used, and due to the size of their required laser power supply and cooling systems. In addition, most pulsed THz systems are designed using free-space delicate optics, making them extremely sensitive to any vibrations, pressures, and torque loadings. Typical prior art THz systems are bulky, heavy, and are not user friendly, even though they may use compact and turnkey pulsed fiber lasers. The demand for THz technology comes from research, industrial, and military applications where the operator is not expected to have experience in advanced optical systems. By its nature, traditional THz time-domain systems are quite complex and difficult to keep optimized. For most field applications, especially for defense applications, a mobile, robust, turnkey, miniature, or handheld THz time-domain spectrometer is essential. Aspects of the present invention provide such a system.

SUMMARY OF THE INVENTION

One aspect of the invention is a method for controlling the polarization of an optical signal including passing a first non-linearly-polarized optical signal having a first polarization ellipticity through a polarization varying device to produce a second non-linearly-polarized optical signal having a second polarization ellipticity greater than the first polarization ellipticity; characterizing the second polarization ellipticity of the second non-linearly-polarized optical signal; and controlling the orientation of the polarization varying device, for example, one or more quarter wave plates, to maintain a predetermined characterization of the polarization ellipticity of the second polarization ellipticity of the second non-linearly-polarized optical signal. In one aspect, characterizing the second polarization ellipticity of the second non-linearly-polarized optical signal comprises isolating at least two polarization components from the second non-linearly-polarized optical signal and, for example, comparing their intensity. In another aspect, controlling the orientation of the polarization varying device comprises controlling the orientation of the polarization varying device as a function of the difference in the intensity of the polarization components.

Another aspect of the invention is an apparatus for controlling the polarization of an optical signal including a polarization varying device adapted to change a first non-linearly polarized optical signal having a first polarization ellipticity passed there through to a second non-linearly polarized optical signal having a second polarization ellipticity, greater than the first polarization ellipticity, for example, one or more quarter wave plates; means for characterizing the second polarization ellipticity of the second non-linearly polarized optical signal; and means for controlling the orientation of the polarization varying device to maintain a predetermined characterization of polarization ellipticity for the second polarization ellipticity of the second non-linearly polarized optical signal. In one aspect, the means for characterizing the second polarization ellipticity of the second non-linearly polarized optical signal comprises means for isolating at least two polarization components from the second non-linearly polarized optical signal. In another aspect, the apparatus further comprises a device adapted to non-linearly polarize a linearly polarized signal to provide the first non-linearly-polarized optical signal, for example, an electro-optical crystal that exhibits the Pockels effect.

Another aspect of the invention is an electro-optical apparatus for characterizing an electromagnetic field, the electro-optical apparatus including an electro-optic crystal positioned so that the electromagnetic field passes therethrough, thereby changing the birefringment of the electro-optical crystal; means for generating an optical probe signal to impinge the electro-optic crystal substantially simultaneous with the electromagnetic field passing therethrough, thereby modulating the polarization of the optical probe signal; polarization varying means for varying the polarization of the modulated optical probe signal; and detecting means for determining polarization modulation of the modulated optical probe signal; means for varying the operation of the polarization varying means in response to the polarization modulation of the modulated probe signal; and means for characterizing the electromagnetic field by evaluating the polarization modulation of the optical probe signal. In one aspect, the polarization varying means comprises means for varying a polarization ellipticity of the modulated optical probe signal. In another aspect, the means for varying the polarization ellipticity of the modulated optical probe signal comprises at least one wave plate, for example, at least one quarter wave plate.

Another aspect of the invention is a method for characterizing an electromagnetic field, the method including positioning an electro-optic crystal wherein the electromagnetic field passes therethrough, thereby changing a birefringment of the electro-optical crystal; generating an optical probe signal and impinging the electro-optic crystal substantially simultaneous with the electromagnetic field passing therethrough, thereby modulating the polarization of the optical probe signal; varying the polarization of the modulated optical probe signal, for example, with at least one quarter wave plate; detecting the polarization modulation of the modulated optical probe signal; controlling the varying of the polarization of the modulated optical probe signal, that is, the quarter wave plate, in response to the detected polarization modulation of the modulated probe signal; and characterizing the electromagnetic field by evaluating the polarization modulation of the optical probe signal. In one aspect, varying the polarization of the modulated optical probe signal comprises varying a polarization ellipticity of the modulated optical probe signal. In another aspect, detecting comprises isolating at least two polarization components from the modulated optical probe signal and by passing the modulated probe signal through a Wollaston prism.

A still further aspect of the invention is an electro-optical apparatus for exposing a target to electromagnetic radiation, the apparatus including a housing; a source of electromagnetic radiation mounted in the housing; a cavity in the housing positioned in a path of the electromagnetic radiation; a modular optical device removably-mounted in the housing cavity, the modular optical device adapted to receive the electromagnetic radiation and expose a target to beam of the electromagnetic radiation to produce a modulated beam of electromagnetic radiation; and means for analyzing the modulated beam of electromagnetic radiation to characterize the target. In one aspect, the electromagnetic radiation comprises a terahertz beam wherein the source of electromagnetic radiation comprises a source of terahertz radiation. In another aspect, the terahertz detector comprises an electro-optical crystal. IN another aspect, the source of electromagnetic radiation comprises a pump laser beam, a probe laser beam, and a source of terahertz radiation activated by the pump laser beam, and wherein the means for analyzing the modulated terahertz beam comprises means for directing the probe laser beam and the modulated terahertz beam through the electro-optical crystal.

A still further aspect of the invention is a method for analyzing a target with electromagnetic radiation, the method including providing an apparatus having a housing, a source of electromagnetic radiation mounted in the housing, and a cavity in the housing positioned in a path of the electromagnetic radiation; inserting a removably mounted modular optical device into the housing cavity, the modular optical device adapted to receive the electromagnetic radiation and expose a target to a beam of the electromagnetic radiation to produce a modulated beam of electromagnetic radiation; and analyzing the modulated beam of electromagnetic radiation to characterize the target. In one aspect, inserting the removably mounted modular optical device into the housing cavity comprises inserting a first removably mounted modular optical device into the housing cavity adapted to expose the target to a first beam of electromagnetic radiation, and wherein the method further includes removing the first removably mounted modular optical device from the housing cavity; and inserting a second removably mounted modular optical device, different from the first removably mounted modular optical device, into the housing cavity, the second removably mounted optical device adapted to receive the electromagnetic radiation and expose the target to a second beam of the electromagnetic radiation, different from the first beam of electromagnetic radiation.

A further aspect of the invention is a modular optical device removably mountable in a housing having a source of terahertz radiation and a terahertz radiation detector, the modular optical device including a frame adapted to removably engage the housing; means for receiving the terahertz radiation from the source of terahertz radiation; means for exposing a target to a beam of the terahertz radiation to produce a modulated beam of electromagnetic radiation; means for receiving the modulated beam of terahertz radiation from the target; and means for directing the modulated beam of terahertz radiation to the terahertz radiation detector in the housing. In one aspect, the means for receiving the terahertz radiation from the source of terahertz radiation comprises one of a mirror, a lens, a diffuser, and a collimator. In another aspect, the means for exposing the target to the beam of the terahertz radiation comprises one of a mirror, a lens, a diffuser, and a collimator.

Another aspect of the invention is a sample holder adapted to expose a sample to a beam of electromagnetic radiation, the sample holder including a housing having substantially closed ends, a substantially closed bottom, an open top for receiving the sample into an internal cavity, and opposing sides having apertures therein into the internal cavity; and means for occluding the open top. In one aspect, the closed ends comprise structures adapted to be received by a sample holder mounting device. In another aspect, the means for occluding the open top comprises a cover adapted to engage the housing. In another aspect, the means for occluding the open top comprises a hardenable fluid, such as, an epoxy, a silicone, a putty, or a wax.

A further aspect of the invention is a radiation source mounting arrangement, for example, a THz source mounting arrangement, including a mounting plate having an aperture positioned to pass a radiation-source-activating laser beam, at least one ground contact, and a plurality of energizable contacts; and a base plate removably mounted to the mounting plate, the base plate having an aperture positioned to pass the source-activating laser beam and a plurality of electrical contacts adapted to contact the at least one ground contact and at least one of the plurality of energizable contacts on the mounting plate to energize a radiation source mounted to the base plate. In one aspect, the removably-mounted base plate is removably mountable to the mounting plate in a plurality of orientations relative to the mounting plate wherein the radiation source assumes a plurality of orientations. In another aspect, the plurality of energizable contacts in the mounting plate comprises a plurality of sleeves and the plurality of electrical contacts on the base plate comprise a plurality of pins engagable with the plurality of sleeves.

A further aspect of the invention is a method of mounting a radiation source, for example, a THz source, including providing a mounting plate having an aperture positioned to pass a radiation source-activating laser beam, at least one ground contact, and a plurality of energizable contacts; providing a base plate having an aperture positioned to pass the source-activating laser beam and a plurality of electrical contacts to energize a radiation source mounted to the base plate; and mounting the base plate to the mounting plate wherein the electrical contacts on the base plate contact the at least one ground contact and at least one of the plurality of energizable contacts on the mounting plate. In one aspect, mounting the base plate to the mounting plate comprises mounting the base plate to the mounting plate wherein the base plate and the terahertz source are mounted in a first orientation relative to the mounting plate, and wherein the method further includes removing the base plate from the mounting plate; and remounting the base plate to the mounting plate wherein the base plate and the radiation source are mounted in a second orientation, different from the first orientation, relative to the mounting plate.

These and other aspects, features, and advantages of this invention will become apparent from the following detailed description of the various aspects of the invention.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

FIGS. 16, 17, an 18 are a front view, a top view, and a side elevation view, respectively, of the sample holder shown in FIG. 15.

FIG. 20 is a perspective view of a sample holder mounting according to another aspect of the invention.

FIG. 21 is a perspective view of a sample holder cover according to an aspect of the invention.

FIG. 22 is a perspective view of a radiation source mounting arrangement according to another aspect of the invention.

FIG. 23 is an exploded perspective view of the mounting arrangement shown in FIG. 22.

FIGS. 27 and 28 are a top plan and a side elevation view, respectively, of the mounting plate shown in FIGS. 22 and 23.

FIG. 29 is a schematic plan view of another radiation source mounting arrangement according to another aspect of the invention.

FIGS. 30A and 30B are a top plan view and a side elevation view, respectively, of another radiation source mounting arrangement according to another aspect of the invention.

DETAILED DESCRIPTION

Figure 1:
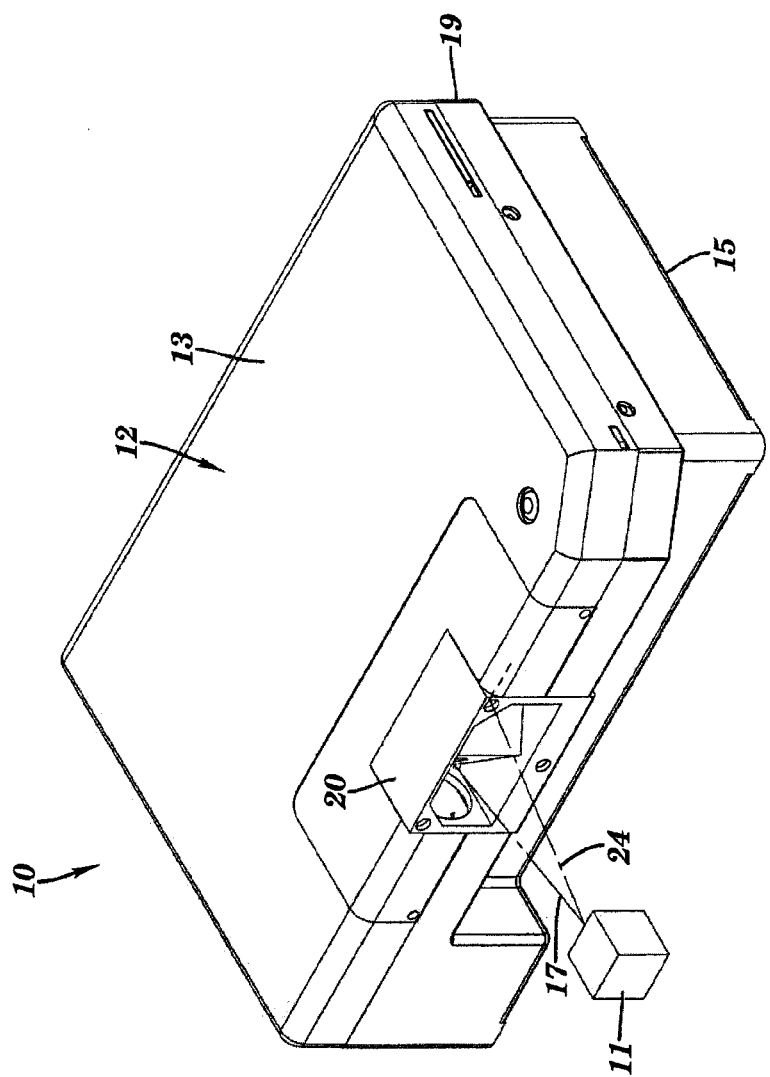
FIG. 1 is a perspective view of an electro-optical apparatus for exposing a target to free-space electromagnetic radiation according to one aspect of the invention.
Figure 2:
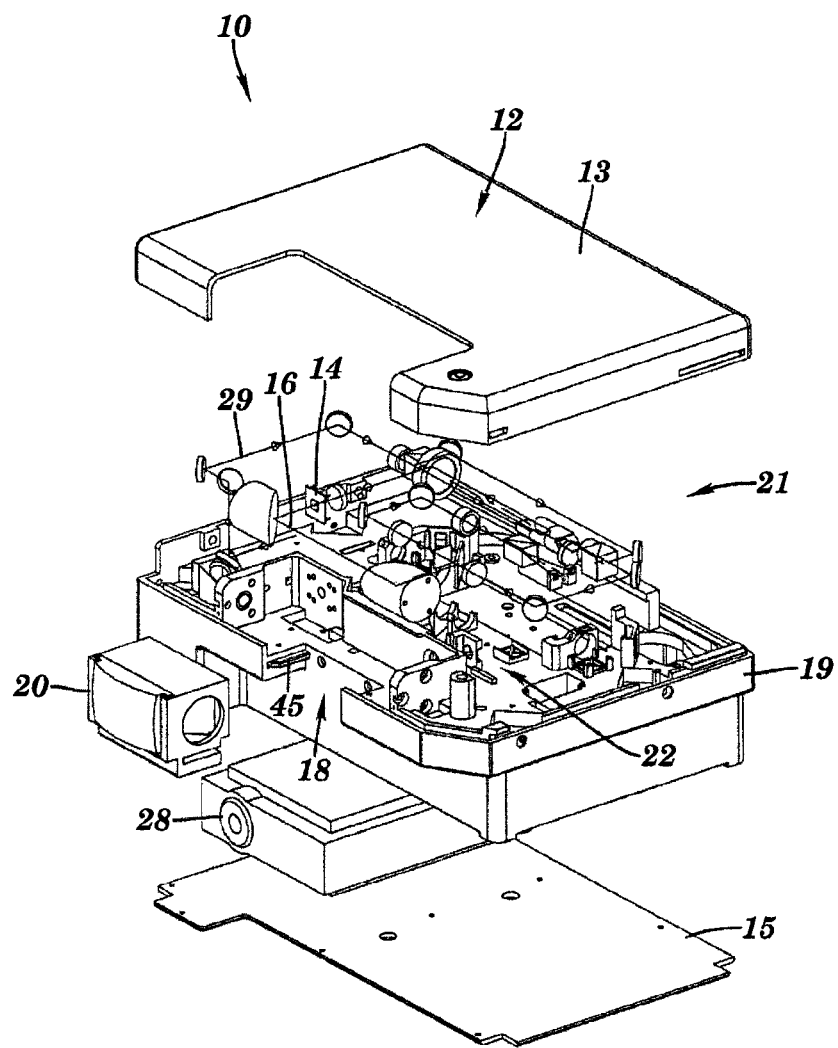
FIG. 2 is an exploded perspective view of the apparatus shown in FIG. 1.

FIG. 1 is a perspective of an electro-optical apparatus 10 for exposing a target (not shown) to free-space electromagnetic radiation according to one aspect of the invention. Though aspects of the invention may be applied a broad range of electromagnetic radiation, aspects of the invention are particularly suitable for the generation, handling, and detection of electromagnetic radiation in a range between between about 300 gigahertz ($3 \times 10^{11}$ Hz) and about 3 terahertz ($3 \times 10^{12}$ Hz), more particularly in the range of about 10 gigahertz to about 5 terahertz, that is, radiation typically referred to as "Terahertz (THz) radiation" or "T rays." For example, see U.S. Pat. No. 5,952,818 of Zhang, et al, the disclosure of which is incorporated herein in its entirety, for the disclosure of related use and manipulation of THz radiation. FIG. 2 is an exploded perspective view of the apparatus 10 shown in FIG.

1. Aspects of the apparatus 10 shown in FIGS. 1 and 2 are marketed under the name "Mini-Z" by applicants.

As shown in FIGS. 1 and 2, according to aspects of the invention, apparatus 10 typically includes a housing 12, a source 14 of electromagnetic radiation 16 mounted in housing 12, a cavity 18 in housing 12 positioned in a path of the electromagnetic radiation 16, a modular optical device 20 removably-mounted in the housing cavity 18, and means 22 for analyzing the modulated beam of electromagnetic radiation to characterize a target 11 (see FIG. 1). Housing 12 may include a removable top cover 13, a removable bottom cover 15, and a chassis 19 upon which optical components 21 may be mounted. According to aspects of the invention, the modular optical device 20 is adapted to receive the electromagnetic radiation 16 and expose target 11 to a beam of electromagnetic radiation 17 to produce a modulated beam of electromagnetic radiation 24 (see FIG. 1). Housing 12 typically may also include a power supply (not shown), a laser beam source 28 providing a laser beam 29 directed toward the source 14 of electromagnetic radiation 16, and associated controllers and processors, user input and output ports, and related electronics (not shown), as is typical in the art. Typical sources 14 of electromagnetic radiation 16 and means 22 for analyzing modulated beams 24 of radiation will be discussed in detail below. A detailed discussion of the various modular optical devices 20 that may be used according to aspects of the invention follows.

Apparatus 10 is adapted to produce a beam of electromagnetic radiation 16, for example, a THz beam, which is manipulated by optical device 20 to expose a sample 11, for example, a sample under test, to the radiation beam 17. Optical device 20 may be any device that is adapted to receive beam 16 and direct beam 17, with or without further modification, upon sample 11. In one aspect of the invention, optical device 20 may also be adapted to receive a reflected or transmitted beam 24 from sample 11, and direct the beam 24 into housing 12, for example, for further processing, for instance, directed to a THz beam detector in housing 12.

According to aspects of the invention, optical device 20 may be replaceably mounted in housing 12, for example, where optical device 20 may be easily removed for cleaning or other servicing, replaced with a new device 20, or replaced with a different device 20' having different optical characteristics than optical device 20. For example, in one aspect, optical device 20 may be removed for servicing or replacement without requiring realignment of the associated optics, for example, without realignment of the optics associated with the THz generation and/or detection. One typical modular optical device 25 that may be used in apparatus 10 according to aspects of the invention is illustrated in FIGS. 3-6.

Figure 3:
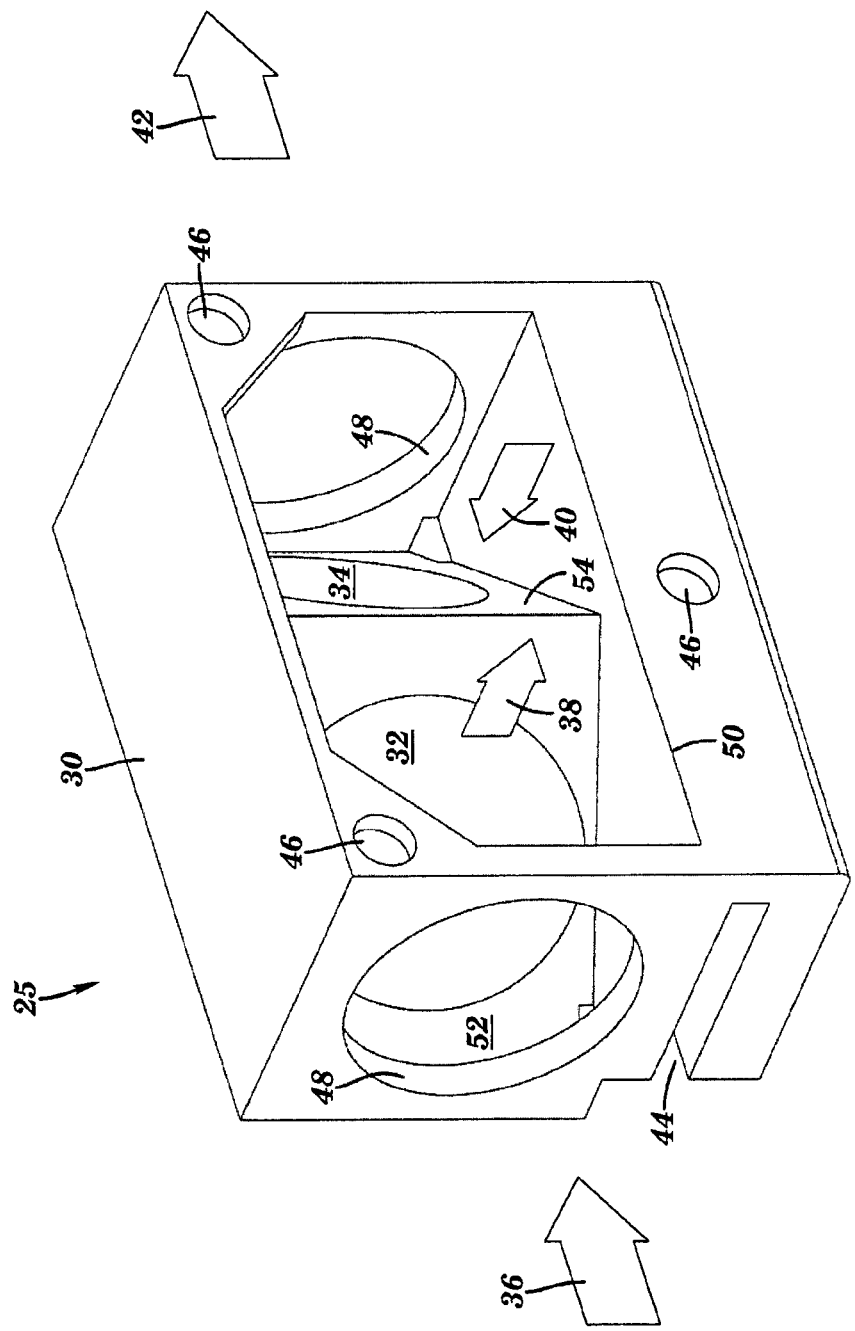
FIG. 3 is a perspective view of a modular optical device adapted to be removably mountable in the apparatus shown in FIGS. 1 and 2.
Figure 6:
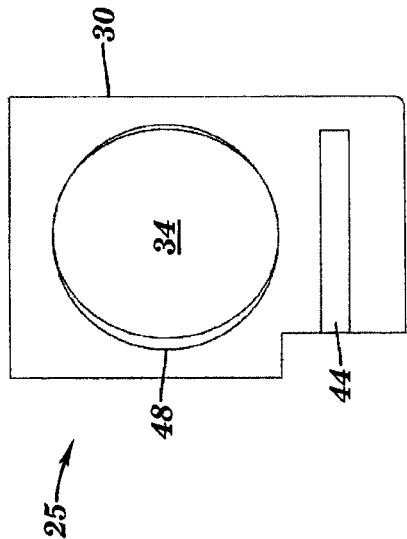
FIG. 6 is a side elevation view of the optical device shown in FIGS. 3-5.
Figure 5:
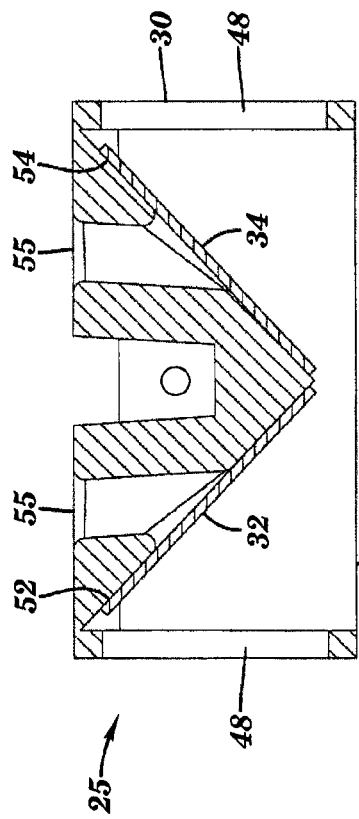
FIG. 5 cross sectional view of the optical device shown in FIGS. 3 and 4 as viewed along section lines 5-5 in FIG. 4.
Figure 4:
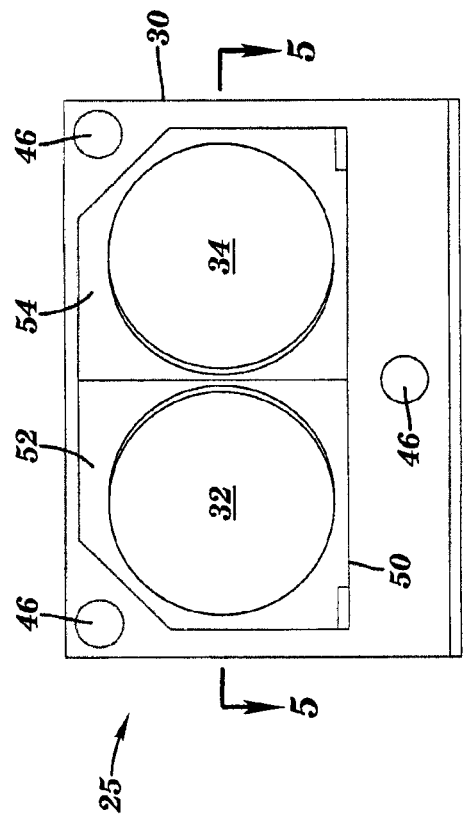
FIG. 4 is a front elevation view of the optical device shown in FIG. 3.

FIG. 3 is a perspective view of modular optical device 25 that can be used for optical device 20 and is removably mountable in the apparatus 10 shown in FIGS. 1 and 2. FIG. 4 is a front elevation view of the device 25 shown in FIG. 3. FIG. 5 cross sectional view of the device 25 shown in FIGS. 3 and 4 as viewed along section lines 5-5 in FIG. 4. FIG. 6 is a side elevation view of the modular optical device 25 shown in FIGS. 3-5. Optical device 25 typically includes a housing 30 and may include one or more optical surfaces, for example, one or more surfaces at least partially reflective or manipulative of the radiation introduced to device 25. For instance, as shown in FIGS. 3-6, in one aspect of the invention, optical device 25 may include a first reflective surface 32 and a second reflective surface 34. Reflective surfaces 32 and 34 may be at least partially reflective, for example, surfaces 32 and/or 34 may provide as least some transmission or beam splitting function to the incident radiation. Surfaces 32 and/or 34 may also be substantially totally reflective to the incident radiation; for example, surfaces 32 and 34 may comprise optical mirrors, for example, mirrors made from aluminum, indium-tin oxide (ITO) glass, or their equivalent.

As shown in FIG. 3, according to one aspect of the invention, reflective surface 32 in optical device 25 is positioned and oriented to receive a beam of electromagnetic radiation 36 (for example, beam 16 shown in FIG. 2) and reflect at least some of the beam 36 as a redirected beam 38 toward a target (not shown), for example, a sample under test. In one aspect, modular device 25 is adapted to redirect beam 36, for example, a THz beam, to beam 38 toward a target. However, in another aspect, optical device 20 may also be adapted to receive a beam 40 from an external source and by means of reflective surface 34 reflect at least some of beam 40 out of housing 30 as beam 42, for example, toward one or more detectors, for instance, one or more detectors located in housing 12 of apparatus 10. In another aspect of the invention, optical device 25 may be adapted to reflect at least some of beam 36 and receive and reflect at least some of beam 40, for example, a beam reflected from a target illuminated by beam 38, and by means of reflective surface 34 reflect at least some of beam 40 out of housing 30 as beam 42, for example, toward one or more detectors, for instance, one or more detectors located in housing 12 of apparatus 10. In other words, device 25 may be adapted to generate beam 38 or receive beam 40 or generate beam 38 and receive beam 40.

Housing 30 of device 25 may be adapted to engage housing 12 of apparatus 10, for example, releasably engage housing 12 whereby optical device 25 may be removed from housing 12 as needed. Typically, housing 30 may include one or more indentations and/or projections adapted to engage corresponding projections and/or indentations in housing 12. Though many different types and sizes of indentations or projections may be used to engage device 25 with apparatus 10, in one aspect of the invention, device 25 may include one or more slots 44 adapted to engage one or more rails or projections 45 on housing 12 (see FIG. 2). Housing 30 may also include one or more through holes 46 for retaining device 25 in housing 12, for example, by mechanical fasteners, such as, bolts or screws.

Housing 30 may also be adapted to permit transmission of beams 36, 38, 40, and 42 with little or no obstruction. For example, housing 30 may include at least one aperture 48 positioned to allow transmission of radiation beam 36, but typically two apertures 48 are provided to allow transmission of beams 36 and 42. In addition, housing 30 may also include at least one aperture 50 positioned to allow transmission of beam 38, but typically two apertures 50 are provided or one large aperture 50 is provided to allow transmission of beams 38 and 40.

Housing 30 may also be adapted to support any optical surfaces or optical modification devices positioned in optical device 25. For example, optical device 25 may include supports and/or positioning means, for example, adjustable positioning means, for reflective surface 32 and/or 34. As shown in FIGS. 3-6, in one aspect, optical device 25 may include at least one optical support or mounting surface 52 and/or 54 for locating and supporting reflective surfaces 32 and 34. As shown, in one aspect, surfaces 52 and 54 may be provided by a prismatic or wedge-shaped structure. Other means of supporting and/or positioning reflective surfaces 32 and 34 may also be provided, for example, conventional optical retainers or holders. Housing 30 may also include one or more holes 55 (see FIG. 5), for example, directed through surfaces 52 and 54, that may be used to assist in the alignment of module optic 25, for example, the alignment with the desired target. For instance, light sources, such as, laser diodes, may be positioned in holes 55 and directed to illuminate a target to assist in alignment of optic module 25 with the target.

In one aspect, optical device 25 may also modify beam 36 and/or beam 42. For example, in one aspect, optical device 25 may include a device that collimates, focuses, diffuses radiation beam 36, 38, 40, and/or 42. For instance, in one aspect, a lens, diffuser, or collimator may be positioned in one or more of apertures 48 to focus, diffuse, or collimate beams 36 and/or 42. In another aspect, optical device 25 may also modify beam 38 and/or beam 40. For example, in one aspect, optical device 25 may include a device that collimates, diffuses, or focuses radiation beam 38 and/or 40. For instance, in one aspect, a lens, diffuser, or collimator may be positioned in one or more of apertures 50 to focus, diffuse, or collimate beams 38 and/or 40.

Housing 30 of optical device 25 may be fashioned in any desired shape, for example, any shape that is compatible with engagement with housing 12 of apparatus 10. For example, as shown in FIGS. 3-6, housing 30 may comprise any parallelepiped shape, for example, square or rectangular parallelepiped. Housing 30 may also be pyramidal or spherical in shape.

Housing 30 may be made from metallic or non-metallic materials. For example, housing 30 may be fabricated from one or more of the following metals: iron, steel, stainless steel, aluminum, titanium, nickel, magnesium, brass, bronze, or any other structural metal, or one or more of the following plastics: a polyamide (PA), for example, nylon; a polyamide-imide; a polyethylene (PE); a polypropylene (PP); a polyester (PE); a polytetraflouroethylene (PTFE); an acrylonitrile butadiene styrene (ABS); a polycarbonate (PC); or a vinyl, such as, polyvinylchloride (PVC), among other plastics. Housing 30 may be fabricated by a broad range of conventional processes, for example, by machining, molding, casting, welding, and the like. However, in one aspect, housing 30 may be fabricated by stereolithographic (SLA) methods, for example, stereolithography using a conventional liquid UV-curable photopolymer and a UV laser.

The size of optical device 25 may vary depending upon the size of the apparatus 10 into which device 25 is installed. For example, device 25 may have a length that may vary from about 0.5 inches to about 36 inches, but is typically between about 1 inch and about 5 inches; for example, device 25 may be about 3 inches long. Device 25 may have a width and a height that may vary from about 0.25 inches to about 12 inches, but is typically between about 0.5 inches and about 2 inches; for example, device 25 may have a width and a height of about 1 inch.

Figure 7A:
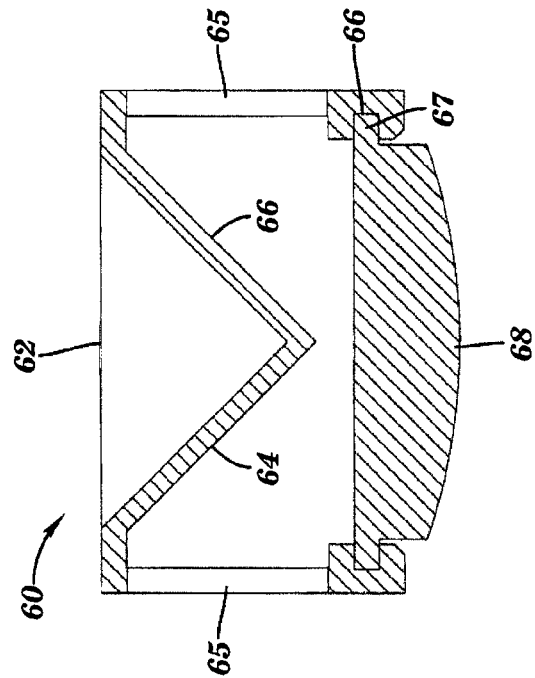
FIGS. 7A and 7B are a perspective view and a cross-sectional view, similar to FIG. 5, respectively, of a modular optical device according to another aspect of the invention.
Figure 7B:
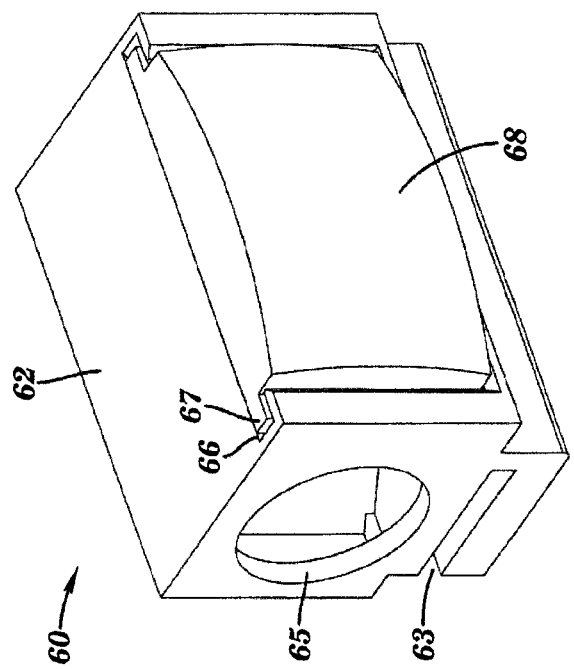

FIGS. 7A and 7B are a perspective view and a cross-sectional view, similar to FIGS. 3 and 5, respectively, of a modular optical device 60 according to a further aspect of the invention. Optical device 60 may be similar to optical device 25 described above, for example, having a housing 62 removably mountable to housing 12, for example, by means of slots 63, and reflective surfaces 64 and 66, similar to surfaces 32 and 34, and at least one aperture 65, similar to aperture 48. However, according to one aspect, optical device 60 may include at least one beam varying structure 68, for example, a lens, diffuser, or collimating device, that varies the path of the beams reflected from surfaces 64 and 66, for example, to and from a target (not shown). For example, optical device 60 may comprise a device similar to device 25 shown in FIGS. 3-6 having a lens 68 positioned in aperture 50 of device 25. As shown in FIGS. 7A and 7B, housing 62 may be adapted to receive beam-varying structure 68, for example, housing 62 may include slots 66 adapted to receive flanges 67 of device 68. Otherwise, device 60 may typically have all the attributes described above for device 25.

Figure 8B:
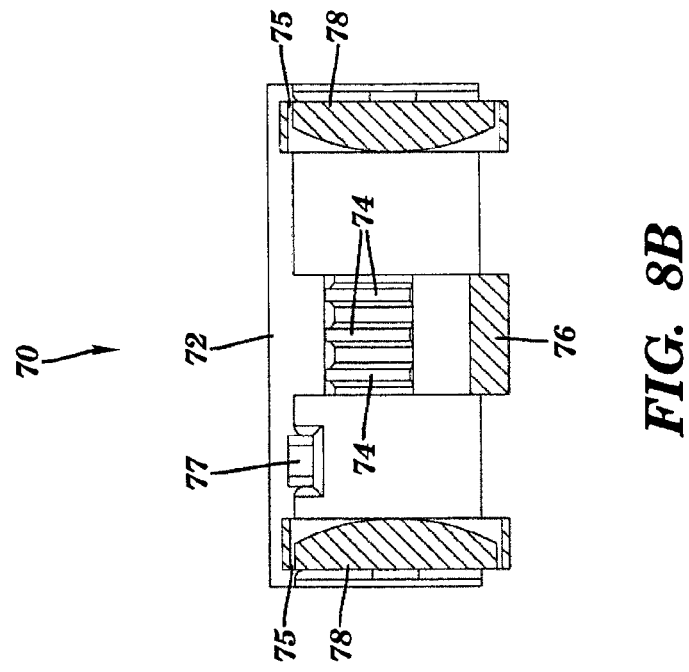
FIGS. 8A and 8B are a perspective view and a cross-sectional view, similar to FIG. 5, respectively, of a modular optical device according to a further aspect of the invention.
Figure 8A:
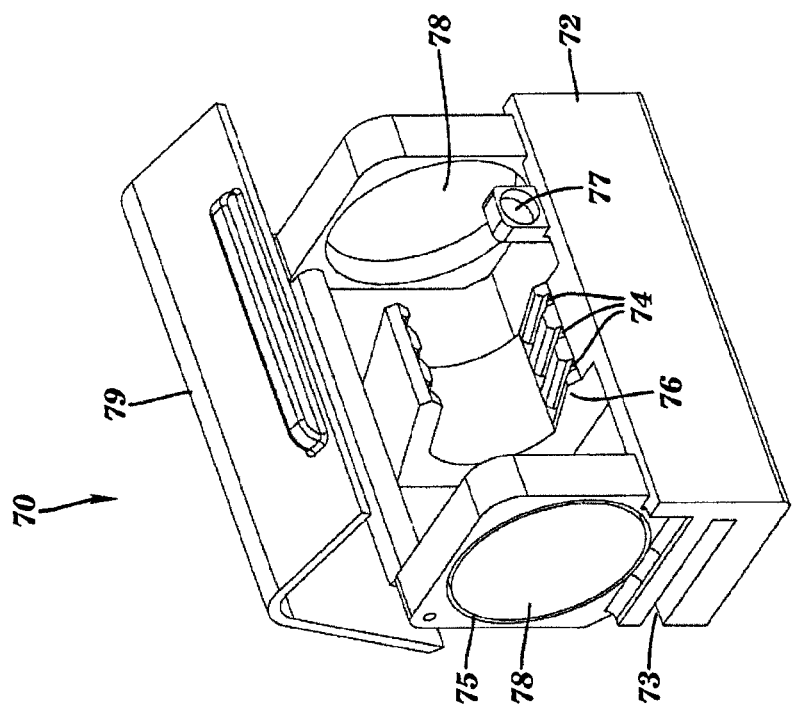

FIGS. 8A and 8B are a perspective view and a cross-sectional view, similar to FIGS. 3 and 5, respectively, of a modular optical device 70 according to another aspect of the invention. Optical device 70 may be similar to optical device 25 described above, for example, having a housing 72 removably mountable to housing 12, for example, by means of slots 73, and at least one aperture 75, similar to aperture 48. However, according to one aspect, optical device 70 may be adapted to receive one or more sample holding devices (not shown), for example, one or more of the sample holding devices 402 shown in FIGS. 15-18 below. Similar to optical device 25, optical device 70 typically includes at least one, but typically two, opposing apertures 75 for transmitting radiation beams, for example, beams 36 and 42 shown in FIG. 3. However, according to the aspect of the invention shown in FIGS. 8A and 8B, optical device 70 is adapted to transmit a beam of radiation through a sample mounted in one or more sample holders. Typically, the one or more sample holders (not shown) are removably mounted in housing 72, for example, by means of one or more indentations and/or projections in the sample holder which cooperate with one or more corresponding projections and/or indentations 74 in housing 72. In the aspect of the invention shown in FIGS. 8A and 8B, housing 72 includes one or more opposing slots 74 into which a sample holder may be removably inserted. In one aspect, projections and/or indentations 74 may be provided on a movable carriage 76. Carriage 76 may be adapted to retain one or more sample holders, or samples without holders, and move to vary the position of the one or more samples, for example, relative to the source of radiation. For example, carriage 76 may translate or rotate within housing 72. Similar to optical devices 25 and 60, optical device 70 may include one or more beam varying devices, for example, a lens, diffuser, or collimating device, that varies the path of the beams directed toward the sample and transmitted through the sample holder, for instance, positioned in at least one of apertures 75. For example, as shown in FIGS. 8A and 8B, optical device 70 may include a lens 78 in each of the apertures 75. As also shown in FIG. 8A, optical device 70 may also include a cover 79, for example, a cover pivotally mounted or hinged to housing 72, for instance, to protect the samples from damage or contamination. Cover 79 may include a cover locking or retaining device, for example, a magnet in a magnet holder 77 that keeps cover 79 closed by interacting with a magnetic material in cover 79. Optical device 70 may also typically have all the attributes described above for device 25.

The aspects of the invention shown in FIGS. 1-8B, provide a turnkey, portable, and fully integrated field detection system, for example, a THz field time-domain detection system, having a system platform with a modular optics front end and modular source. The front end source and detection optical components, for example, the THz source, illumination, and detection components, may typically be sealed from the rest of the system. The optical components may also be purged by different gasses and gaseous substances. Apparatus 10 in FIGS. 1 and 2 may also include an inlet and an outlet for coolant, for example, an inlet and an outlet for gas or liquid coolant to cool the emitter, for example, the THz emitter. Sensors may also be provided to detect internal or external temperature and/or humidity, and the coolant flow regulated accordingly.

Aspects of the invention provide a flexible method and apparatus in which the operator may optionally switch between purged transmission measurements, to stand-off reflection measurements, to custom measurements by replacing optical module 20. The modular laser source allows the user to switch between a compact, low-power pulsed fiber laser to an external laser via an auto-alignment module.

Figure 19:
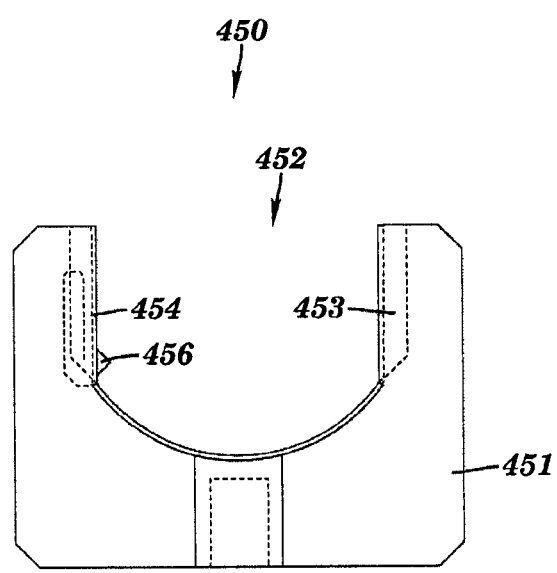
FIG. 19 is a front view of another sample holder mounting according to another aspect of the invention.

Apparatus 10 having modular optics 20, 25, 60, and 70 may be used for a broad range of applications, including, but not limited to:

1. Static, single sample focused transmission, for example, using module 70 shown in FIGS. 8A and 8B with a focusing optic for optic 78.
2. Static, single sample collimated transmission for example, using module 70 shown in FIGS. 8A and 8B with a collimating optic 78 or no optic.
3. Static, multiple samples (one after another) focused transmission, for example, using module 70 shown in FIGS. 8A and 8B with a focusing optic for optic 78 directed toward multiple samples.
4. Static, multiple samples (one after another) collimated transmission, for example, using module 70 shown in FIGS. 8A and 8B with a collimating optic for optic 78 or not optic 78 directed toward multiple samples.
5. Static, multiple samples (sample wheel) focused transmission, for example, using module 60 shown in FIGS. 7A and 7B with a focusing optic for optic 68 directed toward a carousel-type sample holder, as shown in FIG. 19.
6. Static, multiple samples (sample wheel) collimated transmission, for example, using module 60 shown in FIGS. 7A and 7B with a collimating optic for optic 68 directed toward a carousel-type sample holder, as shown in FIG. 19.
7. Dynamic, double sample modulated focused transmission, for example, in which two or more samples may be sequentially exposed to a beam of radiation, for example, in an alternating sequence, a positioning mechanism may be used to alternately introduce the samples to the beam of radiation. Though many mechanisms may be used to provide this alternating exposure, in one aspect, a servomotor, a galvanometer, or a solenoid may be used.
8. Static distance, focused reflection, for example, for example, using module 25 shown in FIGS. 3-6 directed toward a distal target.
9. Static distance, collimated reflection, for example, using module 60 shown in FIGS. 7A and 7B with a collimated optic for optic 68.
10. Static distance, diffused reflection, for example, using module 60 shown in FIGS. 7A and 7B with a diffusing optic for optic 68 directed toward a distal target.
11. Dynamic distance, collimated reflection, for example, using module 60 shown in FIGS. 7A and 7B with a collimating optic for optic 68 reflected off of moving distal target and back to optic 60.
12. Dynamic distance, diffused reflection, for example, using module 60 shown in FIGS. 7A and 7B with a diffusing optic for optic 68 reflected off of moving distal target and back to optic 60.
13. Static distance through gas or liquid cell, collimated transmission, for example, using module 60 shown in FIGS. 7A and 7B with a collimating for optic 68 directed through a gas- or liquid-containing cell positioned in the path of the collimated radiation.

The apparatus 10 shown in FIGS. 1 and 2 may be internally or externally powered, for example, by means of internal power supplies or an external lead to a source of electrical power. The optical modules and the laser source module may also be powered externally, or internally, for example, by means of power connections within apparatus 10. Power may be required to power motors, electronics, and controls. An external connection pass through connection to the back of the apparatus may be provided to provide video or external equipment.

Aspects of the apparatus 10 shown in FIGS. 1 and 2 may typically have broadly ranging dimensions depending upon the application. Apparatus 10 may have a length ranging from about 6 to 36 inches long, typically about 8 to 12 inches long, for example, about 10 inches long. Apparatus 10 may have a width ranging from about 6 to 24 inches wide, typically about 6 to 10 inches wide, for example, about 7 inches wide. Apparatus 10 may have a height ranging from about 2 to 12 inches high, typically about 2 to 4 inches wide, for example, about 3 inches high. Apparatus 10 may weigh no more than 20 pounds, but typically weighs no more than 10 pounds.

Apparatus 10 may also be used in a varied of orientations without change in system operation or system performance. For example, in FIG. 1, apparatus 10 is depicted in one orientation with a long side down. However, apparatus 10 may be positioned on any one of its short sides or even inverted from that shown in FIG. 1 without loss of operation or performance. The housing 12 may include rubber cushions or feet to minimize damage to the housing. Optional handles may also be provided whereby the apparatus 10 may be moved and relocated without change to system operation or performance.

The operation and performance of system 10 may also be continuously monitored statistically during measurements or standby in software. Histograms of, for example, THz amplitude, timing jitter, RMS noise and dynamic range (DNR) and the mean THz waveform and spectrum along with error bars may be provided using at least 250 buffered waveforms. System performance can be described using a statistical method rather than a single waveform, yielding true performance limits. The buffer can be cleared and disabled at the user's will.

Figure 9:
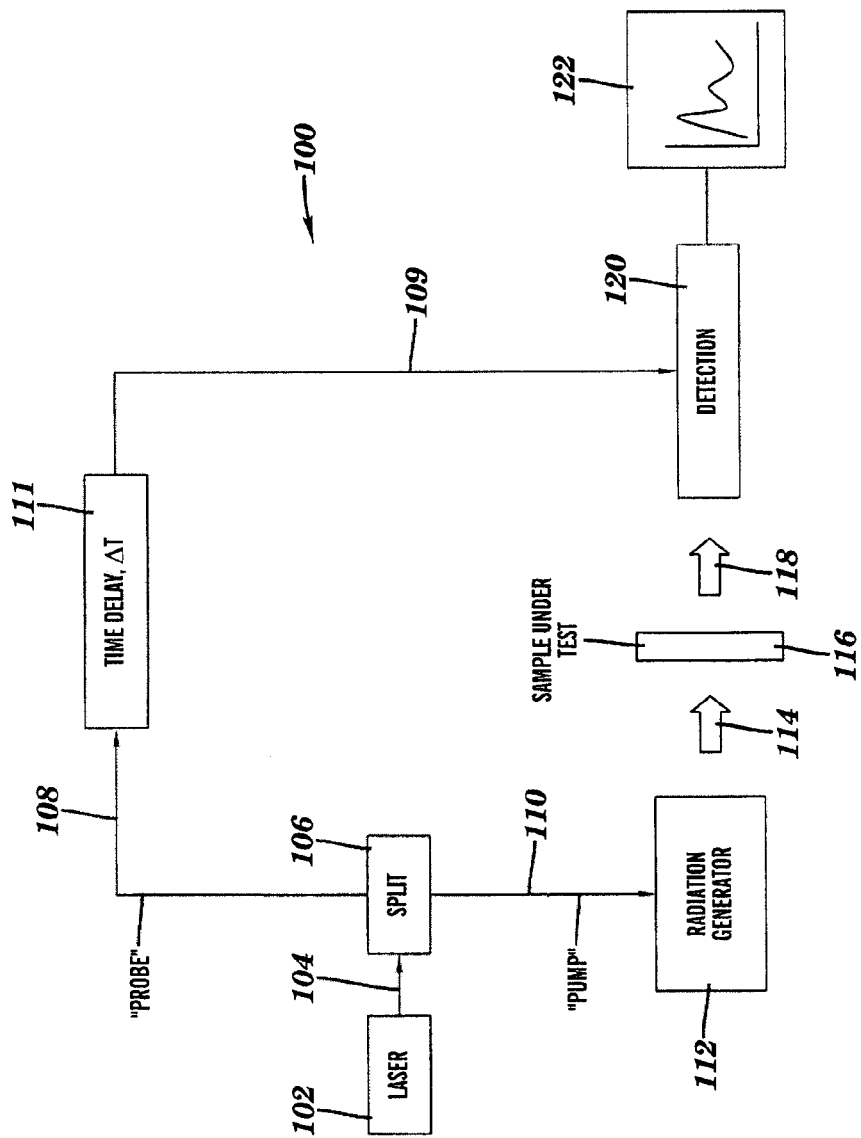
FIG. 9 is a schematic illustration of a radiation source and detection system that be used in the apparatus of FIGS. 1 and 2 according to one aspect of the invention.

FIG. 9 is a schematic illustration of a radiation source and detection system 100 that be used in the apparatus of FIGS. 1 and 2 to optically sample a THz wave according to one aspect of the invention. As is typical in the art, for example, as described in U.S. Pat. No. 5,952,818, system 100 includes a laser source 102, for example, a femtosecond (fs) laser, that produces a laser beam 104, for example, a pulsed laser beam, that is directed to a beam splitting device or beam splitter 106, for example, a polarized beam splitter or beam sampler. As is known in the art, beam splitter 106 divides beam 104 into two beams: a "pump" beam 108 and a "probe" beam 110. As is also known in the art, pump beam 110 may typically be directed to a radiation generator, for example, a THz generator, 112. Radiation generator 112 may be any conventional source of radiation that is activated by a laser, for example, a photoconductive antenna, an electro-optical (E/O) crystal, or a surface emitter, among others. Radiation generator 112 produces a radiation beam 114, for example, a THz beam, which is directed upon a sample under test 116, for example, an explosive or a ERCs or other material under evaluation. In passing through, or reflecting from, sample 116 beam 114 is modulated to produce a modulated beam 118. Modulated beam 118 is then directed to a detection device 120 adapted to detect the modulation of beam 118 to characterize sample 116. Detection device 120 may include a photoconductive antenna or an E/O crystal, among others.

At substantially the same time, probe beam 109 is directed to detection device 120. According to one aspect, detection device 120 typically includes at least one E/O crystal, for example, a zinc-telluride (Zn—Te) crystal, a GaAs crystal, a CdTe crystal, a CdZnTe crystal, or an organic 4-(4-dimethylaminostyryl)-1-methylpyridinium tosylate (DAST) crystal, having refraction properties, for example, birefringence properties, that vary as a function of the electric field to which the crystal is exposed (a phenomenon known as the "Pockels Effect" in the art). When probe beam 109 is also directed through the crystal, either co-currently or counter-currently, the variation in the birefringement of the E/O crystal varies the birefringement of probe beam 109, or the "ellipticity" of probe beam 108, which can be detected. As is known in the art, by determining the variation in the polarization ellipticity of probe beam 108, an indication of the intensity of the electromagnetic field of the modulated beam 118 can be obtained. The detection of the variation of the polarization ellipticity of probe beam 108 can be used to characterize sample 116. Unless otherwise stated, when the term "ellipticity" is used in this specification and the attached claims, the inventors mean "polarization ellipticity."

In order to synchronize the passage of modulated beam 118 and probe beam 109, for example, a pulse beam, through the E/O crystal, the probe beam 108 is typically processed by some form time delay device 111 to produce a time delayed beam 109. The time delay device 111 may typically vary the timing of time-delayed beam 109, typically a pulsed signal, where the pulse of probe beam 109 effectively scans the modulated pulse beam 118 to provide an indication of the variation in the intensity of the electric field and thus an indication of the intensity or shape of the modulated beam 118. For example, in one aspect, time delay device 111 may be a translation stage for translating a single or a double retro-reflector back and fourth while optically sampling the THz waveform. The detection of the variation of the probe beam 109 due to the varying field intensity of modulated beam 118 is typically displayed as a time domain or frequency domain variation on a data processing and output device 122.

Though in the system 100 shown in FIG. 9, the time delay device 111 only operates on the probe beam 108, it will be understood by those in the art that the time delay may also manipulate the pump beam 110 or the probe beam 108 and the pump beam 110. In one aspect of the invention, time delay function 111 may be provided by one or more stationary or translating retroreflectors. For example, in one aspect, probe beam 108 and/or pump beam 110 may be reflected numerous times, for example, 6 times or 8 times, to achieve the desired time delay and synchronization of probe beam 109 with the modulated beam 118.

Figure 10:
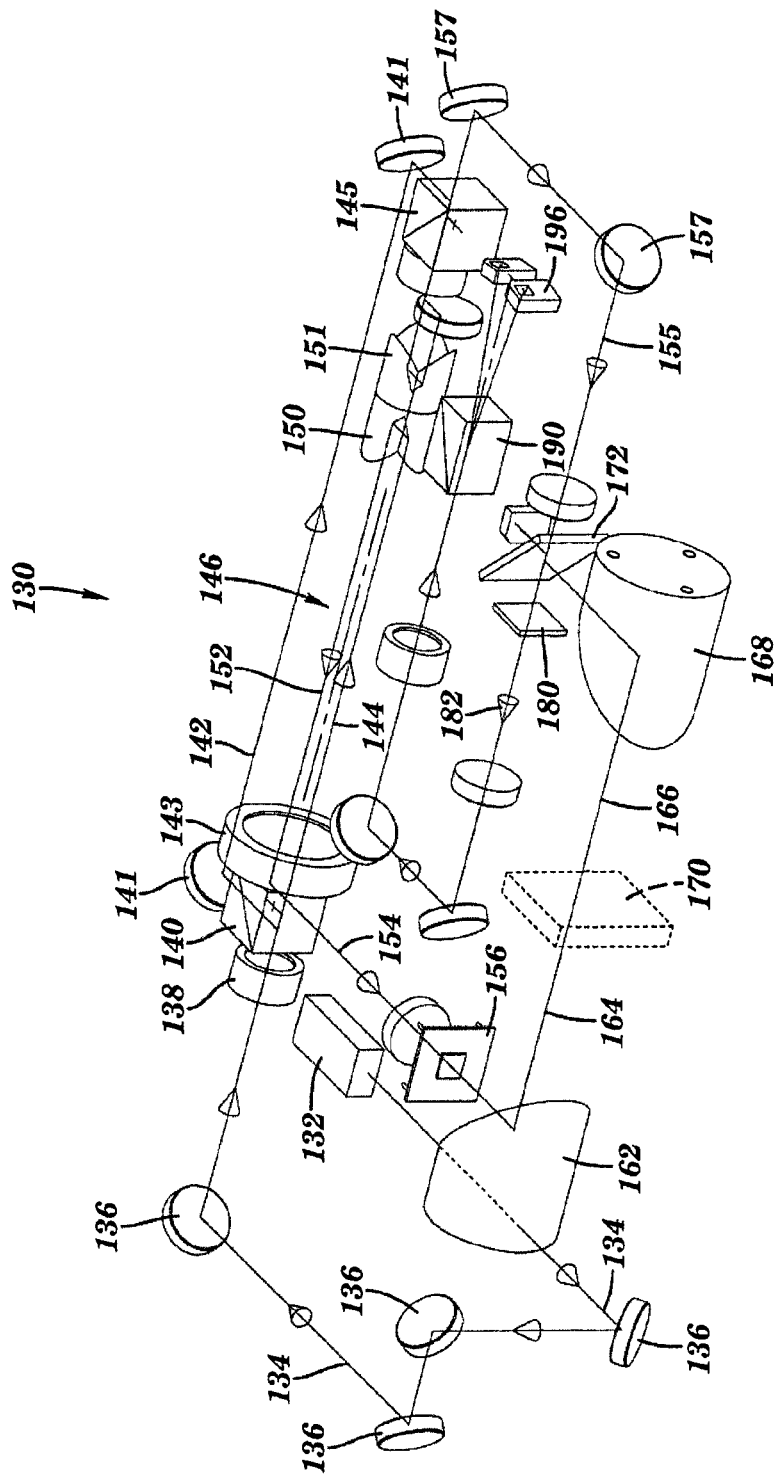
FIG. 10 is a perspective schematic illustration of a radiation source and detection system that can be used to implement the system illustrated in FIG. 9 according to one aspect of the invention.
Figure 11:
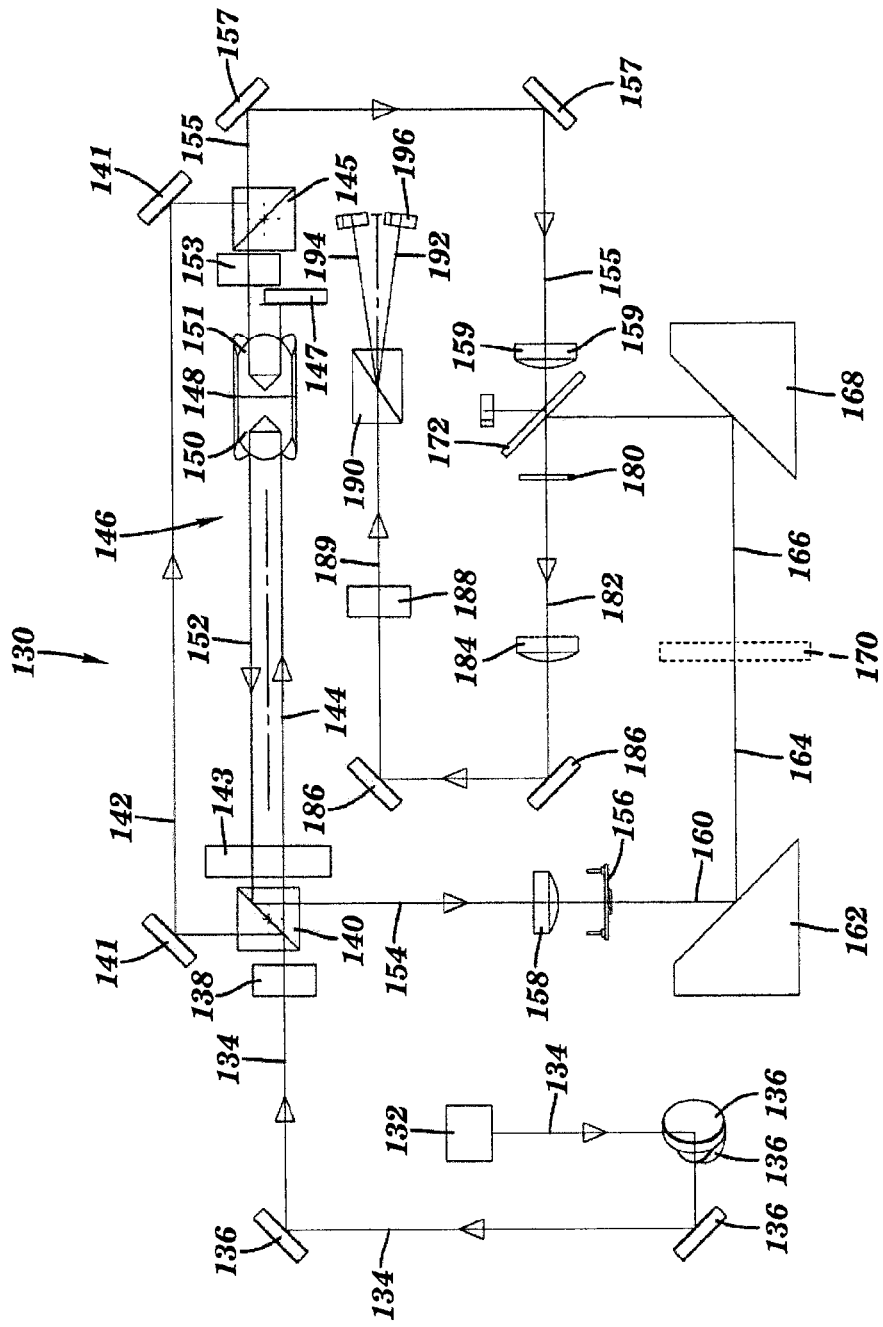
FIG. 11 is a top plan view of the radiation source and detection system shown in FIG. 10.

FIG. 10 is a schematic perspective illustration of a radiation source and detection system 130 that can be used to implement the system illustrated in FIG. 9. Source and detection system 130 may also be used for the source of electromagnetic radiation 16 and means 22 for analyzing the modulated beam of electromagnetic radiation in the apparatus 10 shown in FIGS. 1 and 2 according to one aspect of the invention. FIG. 11 is a top plan view of the system 130 shown in FIG. 10. Though aspects of the invention may be implemented by fiber optics or a combination of fiber optics and free-space optics, in the aspect of the invention shown in FIGS. 10 and 11, a free-space optical layout is shown.

System 130 includes as laser source 132 that provides a laser beam 134. Laser source 132 may be a conventional femtosecond laser as is know in the art. In one aspect, laser source 132 may be a compact pulsed fiber laser, for example, a model AX-20 provided by IMRA America of Ann Arbor, Mich., though other equivalent lasers may be used. For example, laser source 132 may provide 20 mW of average optical power with pulses <100 fs occurring at a 50 MHz repetition rate at a wavelength of about 780 nm. However, laser source 132 with more power may provide improved performance, even with a lower repetition rate. In one aspect, system 130 may include the option to switch between two or more laser sources 132 without any disruption to the optical alignment of laser sources 132 to the rest of the optical components. Laser source 132 may be aligned, for example, with chassis 19 of FIG. 2, with precision pins whereby a high repeatability performance rate is provided should one laser source 132 be replaced with a different laser source. In one aspect, laser source 132 may be a pulsed fiber laser source or a non-pulsed fiber laser source. System 130 may include the capability of employing an external laser source, for example, an external laser source having an iris for course alignment and electromechanical means for fine alignment. The user of system 130 may also be provided with the capability to switch to a higher power external laser when using the system on a bench; however, due to the repeatability of system 130, such as user need have little to no knowledge of optical alignment. Laser source 132 may be provided integrally with system 130, for example, mounted above, below, or adjacent to the components of system 130, or laser source 132 may be provided externally, for example, mounted distal the components of system 130, for instance, outside the housing 12 of system 10 shown in FIGS. 1 and 2.

By means of a series of mirrors 136, for example, adjustable mirrors, laser beam 134 is aligned with the components of system 130. For example, the components of system 130 may be mounted on a common optical plate and mirrors 136 may align beam 134 to a predefined elevation above the optical plate, for example, about 5/16-inch above the optical plate. The aligned laser beam 134 may then be directed to a half-wave plate (HWP) 138 to rotate the polarization of beam 134 before introducing beam 134 to beam splitter 140, for example, a polarizing beam splitter. The function of the HWP 138 is to establish the "pump-probe" intensity ratio after beam 134 is passed beam splitter 140. HWP 138 may be omitted. Beam splitter 140 produces a first "probe" beam 142 and a second "pump" beam 144. In one aspect of the invention, pump beam 144 is directed to quarter wave plate (QWP) 143, or any device that provides the function of QWP, and then to a time delay mechanism 146. In one aspect, QWP 143 linearizes the polarization of the pump beam 144.

Time delay mechanism 146 varies the timing of pump beam 144 whereby the probe beam (that is, the beam generated from probe beam 142) may "scan" the modulated electromagnetic field, for example, the THz wave, generated. According to aspects of the invention, any time delay mechanism 146 may be used to provide this function, for example, one or more translating reflectors. However, in the aspect of the invention shown in FIGS. 10 and 11, time delay mechanism 146 comprises a moveable or translatable carriage 148 having a retroreflector 150. As is known in the art, a retroreflector 150 is a device that reflects an incident beam in a direction parallel and opposite to the direction of the incident beam. In the aspect of the invention shown in FIGS. 10 and 11, retroreflector 150 produces reflected beam 152 parallel and opposite in direction to probe beam 144.

The translation of carriage 148 may be practiced by any conventional means, for example, solenoid, belt, chain, slider, and the like. However, in the aspect of the invention shown in FIGS. 10 and 11, carriage 148 may be translated by two timing pulleys (not shown) and a timing belt (not shown) attached to carriage 148. Carriage 148 may translate along a rail (not shown) or other conventional alignment device. One or more of the timing pulleys may be driven by a compact motor (not shown), the operation of which may be controlled by a motion control circuit.

In the aspect shown in FIGS. 10 and 11, reflected pump beam 152 passes through QWP 143 and beam splitter 140 and is reflected as pump beam 154. Pump beam 154 is directed to emitter 156, for example, a THz emitter. Pump beam 154 may be directed through a lens 158 that focuses the pump beam 154 upon emitter 156. Emitter 156 may be any electromagnetic radiation emitter adapted to emit electromagnetic radiation for use in characterizing a target. In one aspect, emitter 156 may be a THz emitter, for example, a photoconductive antenna, an electro-optical crystal, or a surface emitting emitter. In one aspect of the invention, emitter 156 may be a photoconductive antenna, for example, a photoconductive antenna provided on the antenna mount disclosed and described with respect to FIGS. 20-25 below, though other mountings may be used. As is known in the art, a photoconductive antenna relies on a bias to accelerate generated photocarriers back and forth between electrodes.

The impingement of pump beam 154 upon emitter 156 generates radiation beam 160, for example, a THz pulse. Beam 160 is then directed as needed against a target 170. Target 170 may be any sample under test, for example, an explosive or pharmaceutical. Beam 160 may be modified as desired. For example, beam 160 may be focused by means of a lens upon sample 170. In another aspect, beam 160 may be collimated, for example, by parabolic mirror 162, for example, an off-axis parabolic mirror, to produce collimated beam 164. When beam 160 comprises a THz beam, mirror 162 may be a gold coated parabolic mirror, for example a 1-inch diameter gold coated parabolic mirror that creates a 1-inch diameter collimated THz beam, though the size of beam 164 may vary from about 0.05 inches to about three feet, depending upon the size of the apparatus. Silicon, polyethylene, or any material transparent to THz that can make up a focusing device (lens or mirror) may be used in the absence of parabolic mirrors. Collimated beam 164 may then be directed to target 170. In one aspect, collimated or focused beam 164 may be directed to one of the optical modules 25, 60, or 70 disclosed above.

In one aspect of the invention, in passing through or reflecting from target 170 beam 164 is modulated to modulated beam 166. For example, at least one characteristic of beam 164, for example, its amplitude, frequency, phase, polarization, and polarization ellipticity, among other characteristics, may be varied in passing through or reflecting beam 164 from target 170. According to aspects of the invention, the variation in the characteristic of beam 166 is detectable and at least some characterization of target 170 can be provided. In order to detect a characteristic of modulated beam 166, beam 166 is typically directed toward a detector 180. Though detector 180 may be capable of detecting a broad range of electromagnetic radiation wavelengths, in one aspect of the invention, detector 180 comprises a THz detector. For example, one THz detector that may be used is an E/O crystal, such as ZnTe crystal, a GaAs crystal, a CdTe crystal, a CdZnTe crystal, or an organic 4-(4-dimethylaminostyryl)-1-methylpyridinium tosylate (DAST) crystal, or their equivalent, that exhibits the Pockels effect, that is, the creation of a birefringence, or double refraction, in an optical medium when the medium is exposed to an electric field. An E/O crystal detector typically has a lower demand for precise alignment, which may be preferred when apparatus 10 shown in FIGS. 1 and 2 is used under adverse conditions. However, other detectors may be used, such as a photoconductive antenna or a similar device.

In one aspect of the invention, the modulated beam 166, for example, after passing through a replaceable module, 25, 60, or 70, may be focused an electro-optical (E/O) crystal detector 180 substantially simultaneously with a probe beam 155.

In the aspect of the invention shown in FIGS. 10 and 11, modulated beam 166 may be focused by a mirror 168, for example, a second parabolic mirror, upon a beam splitter 172. Beam splitter 172 is adapted to reflect the radiation of beam 166, for example, THz radiation, and be transparent to optical beams, for example, beam 155, for example, beam splitter 172 may be indium-tin oxide (ITO) glass. Beam splitter 172 reflects at least some of beam 166 to E/O crystal 180.

At substantially the same time, probe beam 155 is also introduced to E/O crystal 180. As is know in the art, probe beam 155 is generated by probe beam 142 generated by beam splitter 140. As shown in FIGS. 10 and 11, probe beam 142 is reflected from beam splitter 140 to one or more mirrors 141 to beam splitter 145, for example, a polarizing beam splitter, where probe beam 142 is directed through QWP 147 to retroreflector 151 also mounted on translating carriage 148. Probe beam 142 is then reflected back through a QWP 153 and beam splitter 145 to emerge as timed delayed probe beam 155. Probe beam 155 is reflected by one or more mirrors 157, for example, adjustable mirrors, through lens 159 where is it focused through beam splitter 172 to merge with the modulated beam, for example, modulated THz beam, 166, and propagate collinearly through E/O crystal 180. As is know in the art, the polarization, for example, the polarization ellipticity, of probe beam 155 is varied by the variation of the birefringence of E/O crystal 180 by the electromagnetic field of modulated beam 160 to produce a modulated probe beam 182, for example, a beam having at least some polarization ellipticity.

Modulated probe beam 182 is then directed to a detector to determine the modulation of probe beam 182 and thus to characterize the modulated beam 166 passed through or reflected from target 170. As shown in FIGS. 10 and 11, modulated probe beam 182 may be focused by lens 184 and directed by one or more mirrors 186 through QWP 188 to further modulate the polarization of beam 182, for example, to vary the polarization ellipticity of beam 182, and produce probe beam 189 having a different polarization than probe beam 182. The polarization components of probe beam 189 may be split by a polarizing beam splitter 190, for example, a Wollaston prism, and the components 192, 194, are directed to the balanced detector 196.

Figure 12:
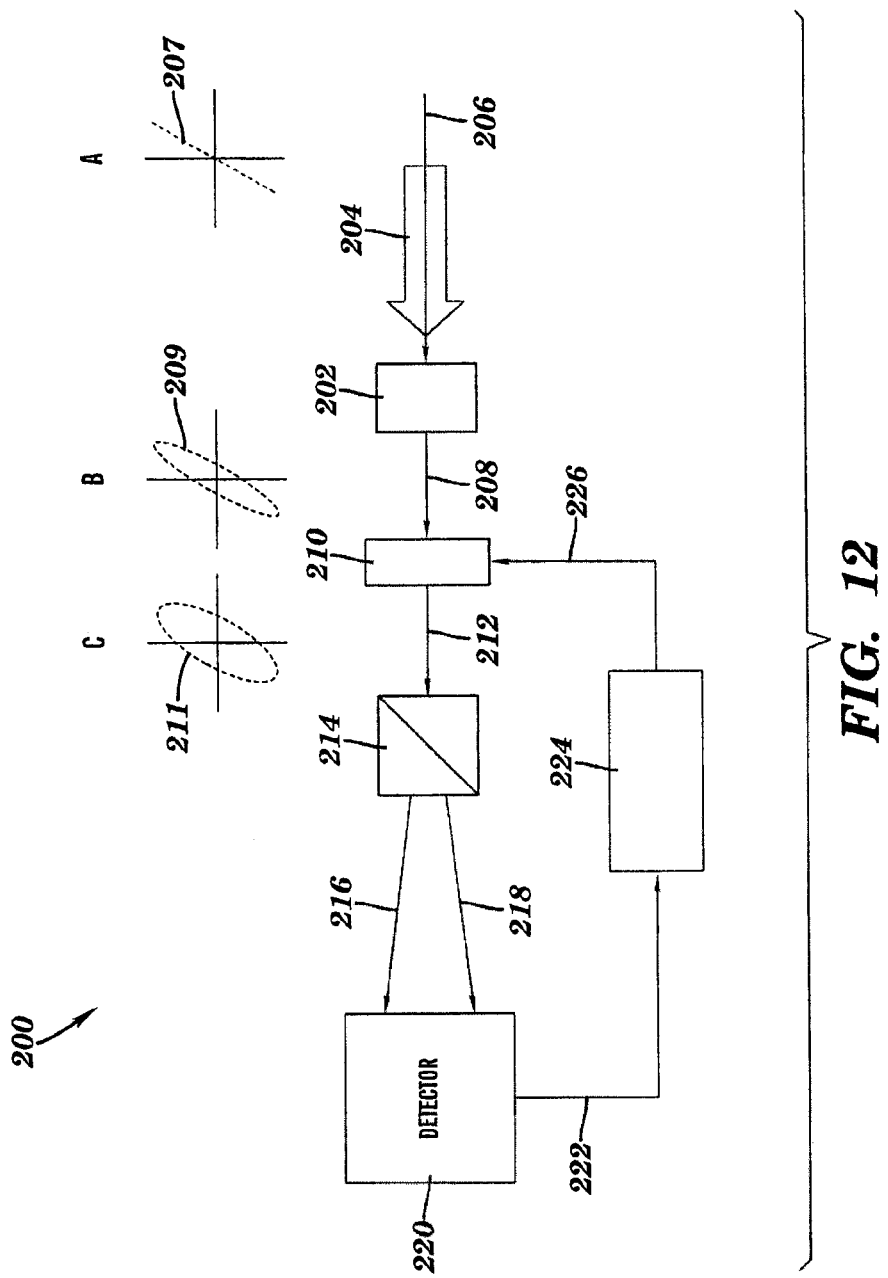
FIG. 12 is a schematic view of a method and apparatus for controlling the polarization of an optical signal according to an aspect of the invention.

FIG. 12 is a detailed schematic view of a method and apparatus 200 for controlling the polarization of an optical signal according to an aspect of the invention. Apparatus 200 and its method of operation is similar to conventional methods of detecting electromagnetic fields, for example, THz fields, (for instance, those methods illustrated in FIGS. 10 and 11 above), but provides an improvement not found in the prior art. As is typical of the art, apparatus 200 includes an electro-optical crystal 202 having the property that the birefringement of crystal 202 varies as a function of the electromagnetic field to which crystal 202 is exposed. For example, crystal 202 may be a ZnTe crystal as described above with respect to detector 180, or its equivalent. According to one aspect of the invention crystal 202 is exposed to an electromagnetic field of electromagnetic radiation beam 204, for example, a THz pulse, whereby the birefringence of crystal 202 is varied. For instance, beam 204 may be a beam similar to the beam 166 generated by apparatus 130 disclosed and described with respect to FIGS. 10 and 11 above. While crystal 202 is exposed to the field provided by beam 204, probe beam 206, for example, the probe beam 155 of apparatus 130 shown in FIGS. 10 and 11, is directed through crystal 202 whereby the polarization of probe beam 206 is varied by the birefringement of crystal 202. For example, beam 206 may typically be a linear, non-polarized laser pulse, for instance as indicated by the line 207 in the polarization diagram A above beam 206 in FIG. 12. After passing through crystal 202, the polarization of beam 206 is varied by crystal 202, for example, whereby a non-linearly polarized beam 208 is produced. As is known in the art, the polarization of beam 208 may be characterized as having at least some "polarization ellipticity," that is, having at least two orthogonal components in the X and the Y planes of a polarization projection plot. One such plot for a non-linearly polarized beam 208 is schematically shown as ellipse 209 in the polarization diagram B in FIG. 12. It will be understood by those in the art that ellipse 209 is not drawn to scale but is simply provided as a relative indication of the variation in polarization of beam 208 compared to beam 206 (and compared to beam 212, discussed below).

According to aspects of the invention, non-linearly polarized beam 208 having polarization ellipticity 209 is then passed through a polarization varying device 210 that is adapted to vary the polarization of beam 208 and generate another non-linearly polarized beam 212. For example, in one aspect, polarization device 210 is adapted to vary a first polarization ellipticity of beam 208 to a second polarization ellipticity, different from the first ellipcity, of beam 212. In one aspect of the invention, polarization device 210 may be one or more wave plates, for example, one or more half-wave plates (HWP) or quarter-wave plates (QWP). A representative plot of the polarization ellipticity of non-linearly polarized beam 212 is schematically shown as ellipse 211 in the polarization diagram C in FIG. 12. As shown schematically in polarization diagrams B and C, the polarization ellipticity 211 of beam 212, in one aspect of the invention, may be greater than the polarization ellipticity 209 of beam 208.

According to aspects of the invention, the polarization of beam 212, for example, as indicated by ellipse 211, may be maintained or varied. For example, in one aspect, the polarization of beam 212 may be maintained to ensure a substantially constant polarization while external factors, such as, temperature, promote the variation of the polarization of beam 212. In another aspect, the variation of beam 212 may be varied as desired, for example, to reduce noise and/or increase signal strength. In one aspect of the invention, the controlling or regulation of the polarization of beam 212 is practiced by controlling or regulating the orientation of polarization varying device 210, for example, as discussed below.

According to aspects of the invention, the polarization, that is, the polarization ellipticity, of the non-linearly polarized beam 212 may be controlled by measuring the polarization of beam 212 and then controlling the orientation of device 210 to maintain or vary the polarization of beam 212. In one aspect of the invention, as shown in FIG. 12, the polarization or polarization ellipticity of beam 212 may be determined by first passing beam 212 through a device 214 adapted to produce at least two polarized beams 216 and 218, that is, the "s" and "p" polarization components. In one aspect of the invention, device 214 may be a Wollaston prism, that is, a device that separates polarized light into two orthogonal, linearly polarized beams. The two polarized beams may then be characterized by detector 220. As is known in the art, detecting the intensity of the polarized beams 216 and 218 or the difference in intensity of the two polarized beams 216 and 218 provides an indication of the polarization of the modulated beam 208, and thus, the intensity of the electric field of modulated beam 204.

According to one aspect of the invention, detector 220 may be a balanced photodiode detector. In the field of the invention, "balance" is defined as the subtraction of the s- and p-polarization component intensities, for example, after the probe beam 206 has interacted with an electromagnetic field of beam 204, for example, a THz field, within electro-optic crystal 202. A benefit of using a balanced photodiode detector is that the laser noise will cancel out completely when the system has zero balance. As the balance drifts from zero, the measured laser noise will increase proportionally to the imbalance, since the imbalanced portion will not cancel out. However, a disadvantage of using balanced detection is that balance point in the electro-optic detection may drift during operation, for example, due to, among other things, temperature variations, probe-beam location shift, room pressure and humidity, and tension in the electro-optic crystal. Aspects of the present invention, overcome these and other disadvantages of the prior art by providing a method and apparatus for "auto balancing" a detection system, such as, auto-balancing the system shown in FIGS. 10 and 11.

As shown in FIG. 12, according to one aspect of the invention, the nature of the polarization components 216 and 218 are characterized by detector 220 and a associated signal 222 corresponding to the characterization of components 216 and 218, for example, their difference, sum, factor, quotient, is forwarded to a control means 224 to generate a control signal 226 by which the operation of polarization varying device 210, for example, a QWP, may be maintained or varied. In one aspect, the polarization varying device 210 may comprise one or more QWPs, and control signal 226 may be provided to maintain or vary the orientation of one or more QWPs 210. The orientation of the one or more QWPs 210 may be varied by rotation along the axis of the QWP or along one or more axes perpendicular to the axis of the quarter wave plate. According the aspect of the invention shown in FIG. 12, a feed back control loop is provided whereby the output 222 of detector 220 may be substantially continuously fed back to the operation of polarization varying device 210 to maintain or vary the polarization of modulated beam 212 as desired. In one aspect, the variation of the polarization, for example, the polarization ellipticity, of the modulated probe beam 212 is controlled to minimize the generation of noise in the detector 220 so that a more reliable characterization of the electromagnetic field provided by beam 204, for example, a THz beam, can be detected and determined.

In one aspect, detector 220 comprises a balanced photodiode detector that outputs a current signal 222 corresponding to the difference in the intensity of polarization components 216 and 218. When an electric field due to beam 204 is present, for example, a THz pulse electric field, the current signal 222 is proportional to the detector loop current. (See U.S. Pat. No. 5,952,818, the disclosure of which is incorporated by reference herein, for further details).

Figure 13:
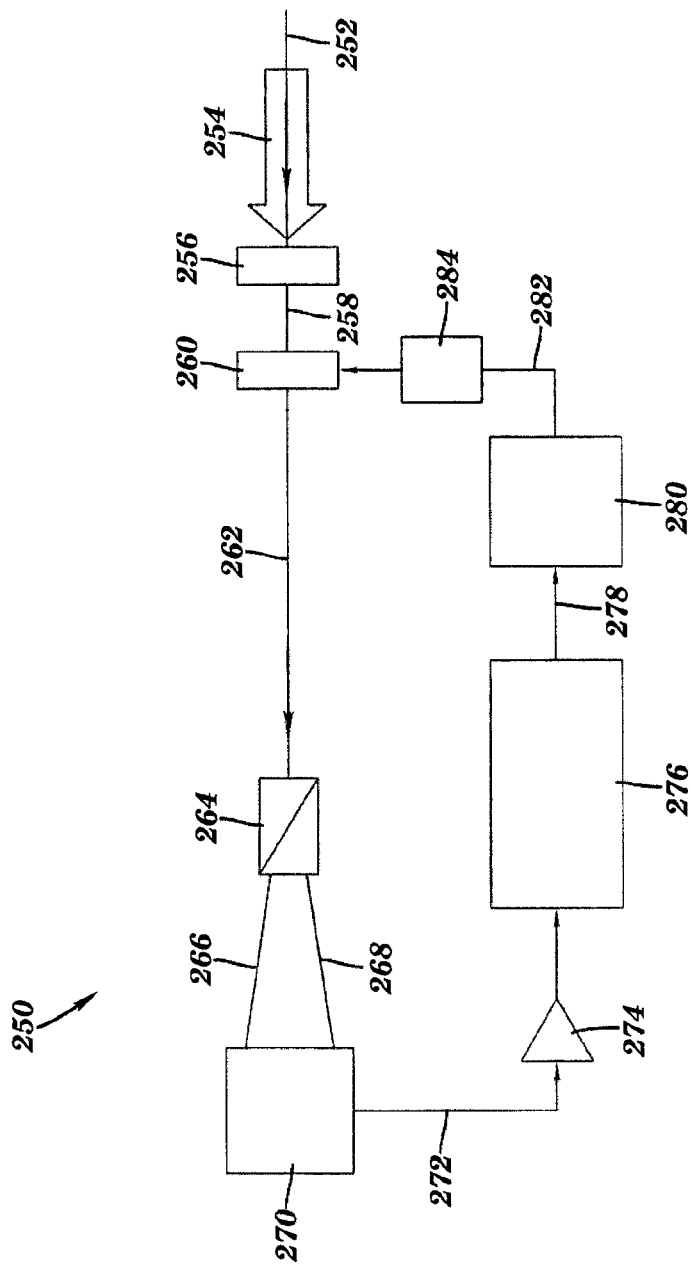
FIG. 13 is a schematic view of a method and apparatus for controlling the polarization of an optical signal according to another aspect of the invention.

FIG. 13 is a detailed schematic view of another method and apparatus 250 for controlling the polarization of an optical signal according to an aspect of the invention. Apparatus 250 and its method of operation are similar to the method and apparatus 200 shown in FIG. 12. Similar to apparatus 200, apparatus 250 includes probe laser beam 252 directed through E/O crystal 256 where it is modulated by an electromagnetic field, for example, a THz electric field, provided by electromagnetic beam 254. E/O crystal 256 may be similar to the E/O crystal described above with respect to E/O crystal 202. The modulated probe beam 258 is directed through a polarization varying device 260, such as, one or more QWPs, which alters the polarization of beam 258 and produces polarization varied beam 262, that is, a beam with varied polarization ellipticity compared to beam 258. Beam 258 is directed to a device 264 adapted to produce at least two polarized beams, such as a Wollaston prism, to isolate two polarization components 266, 268, for example, a horizontal and a vertical polarization component, of modulated probe beam 262.

Polarization components 266 and 268 are directed to a balanced photodiode detector 270.

According to aspects of the invention, the intensity difference between the two beam polarization components 266, 268 is converted to a voltage inside the balanced detector 270. The DC component 272 of this voltage signal is output by detector 270 and passed through an amplifier 274 and then into a controller 276, for example, a microcontroller unit (MCU) with an onboard analog to digital converter. Controller 276 may include software adapted to control signal 278 to control the operation of polarization varying device 260. In one aspect, depending on the detector balance voltage 272, controller 276 may output a control signal to an H-bridge 280 which is adapted to control a motor 284, for example, a DC motor, to control the operation of polarization varying device 260, for example, to rotate one or more QWPs.

According to the aspects of the invention shown in FIGS. 12 and 13, a method and apparatus are provided that automatically balance the polarization components of a modulated probe beam to improve electromagnetic field detection. These methods and apparatus may continuously and automatically adjust field detection, for example, THz field detection, to provide optimal detection. Aspects of the present invention contrast markedly with prior art manual methods.

According to some aspects of the invention, fine adjustment of the polarization of the modulated probe signal may be provided through software. For example, the auto-balancing function shown in FIGS. 12 and 13 may provide a coarse control, while fine control may be provided in controllers 224 or 276, for example, by varying the gain of one of the balanced detectors or subtracting a value from a detector current, among other methods.

Figure 14:
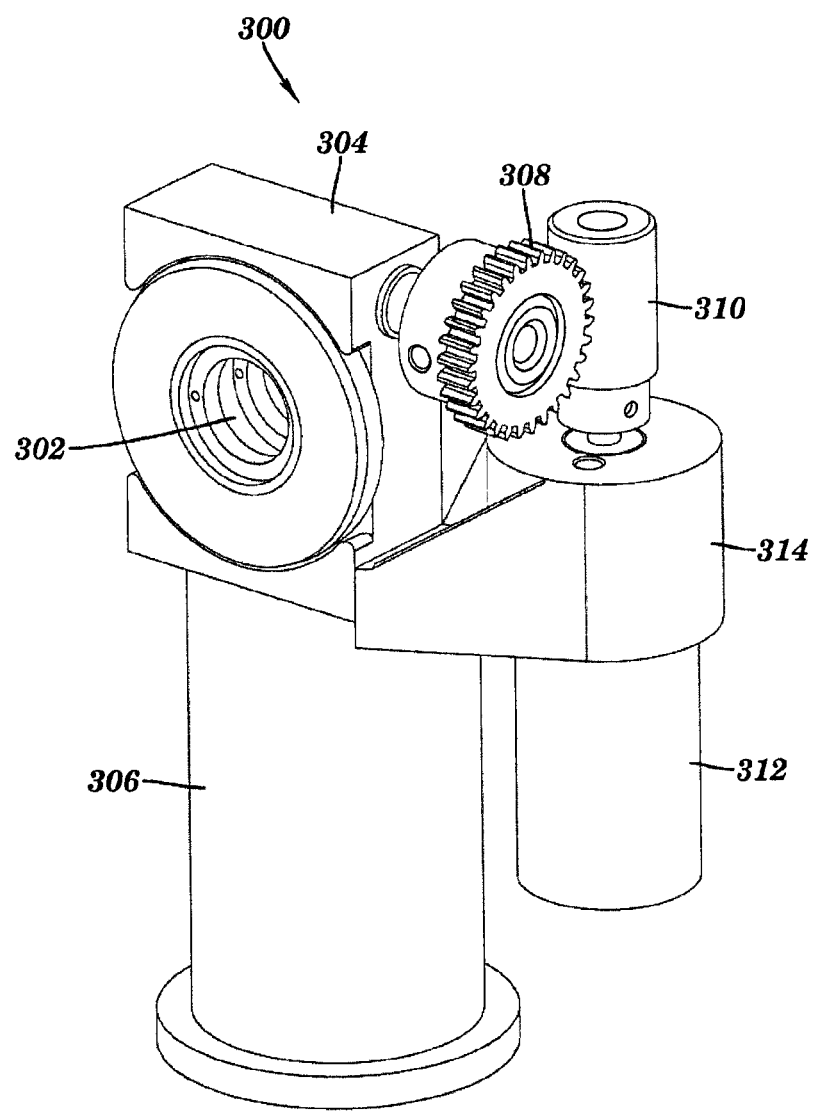
FIG. 14 is a perspective view of an optical mounting that may be used in the practice of the aspects of the invention shown in FIGS. 12 and 13.

FIG. 14 is a perspective view of a typical mounting and drive 300 that may be used to regulate the orientation of a quarter wave plate (QWP) according to one aspect of the invention. Apparatus 300 includes a QWP 302 mounted in an optical rotary stage 304 mounted on a pedestal 306. Though the orientation of QWP 302 may be varied by a broad range of drive mechanism, including belts, gears, chains, galvanometers, translation stages, solenoids, piezo-electric actuators, and the like, in the aspect of the invention shown in FIG. 14, the orientation of QWP 302 is regulated by means of a worm gear drive, having a driven pinion 308 operatively connected to QWP 302 and a driven worm gear 310. Though the driven gear 310 may be rotated by any motive device, in the aspect shown, gear 310 is driven by motor 312, for example, a DC motor. Motor 312 may typically be operated by a motor controller (not shown) and signals from a controller, for example, from a controller such as controllers 224 or 276 in FIG. 12 or 13, respectively. Motor 312 may also be mounted to pedestal 306 by bracket 314.

Figure 15:
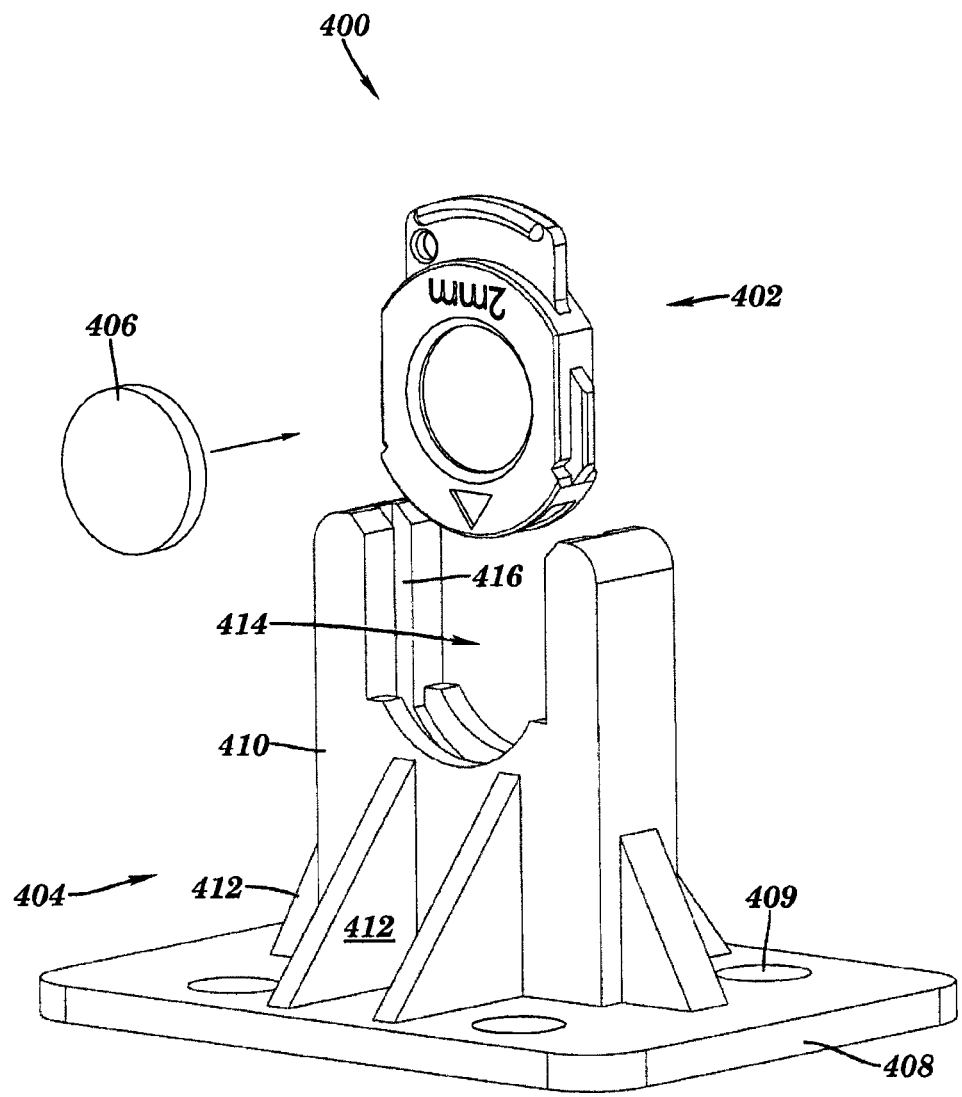
FIG. 15 is a perspective view of a sample holding arrangement according to another aspect of the invention.

FIG. 15 is an exploded perspective view of a sample holding arrangement 400 according to another aspect of the invention. Sample holding arrangement 400 is adapted to expose a sample to a beam of electromagnetic radiation. In the application of various spectroscopy methods, including THz spectroscopy, it is well known in the art that samples under test may be provided in the form of pellets. Pellets typically consist of thin, typically, circular cylindrical samples that can be positioned and illuminated by the desired electromagnetic radiation. For example, typical sample pellets may comprise samples that are compressed into pellets. The compressed samples may be either pure samples of the material to be analyzed or may contain a binding agent, for example, at least some polyethylene or other material substantially transparent to the radiation being used. The binding agent may lessen the sample concentration, but may typically increase the sample rigidity to, among other things, facilitate handling. Typically, some pellets, especially those containing substantially pure samples of the material under test, are thin and brittle, and thus are typically difficult to handle without damaging or breaking the pellet. Though a damaged or broken pellet can be reformed by grinding the broken pellet down into a powder and then reforming the pellet from the powder, damage to the pellet is preferably avoided. Aspects of the invention shown in FIGS. 15-19 overcome these and other disadvantages of handling sample pellets for spectroscopic and related analysis.

Aspects of the invention shown in FIGS. 15-19 also address other concerns when handling samples for spectroscopic analysis, including THz spectroscopy. As is common in the art, samples may be assembled into sample libraries for standardization, documentation, and reference. These sample libraries may not only include samples of multiple compounds, for example, multiple explosives, ERC, or pharmaceuticals, but typically may include multiple samples of single compound, for example, samples that comprise different concentrations of the compound, for instance, for calibrating system selectivity. Since such library samples may be repeatedly handled for mounting, analysis, and storage, a standard method for handling and mounting such samples is desirable. In addition, some samples may not only consist of solid compressed powder pellets, but may include liquid samples and gaseous samples as well. Aspects of the present invention shown in FIG. 15-19 also provide an effective means for handling, mounting, analyzing, and storing samples that address these and other disadvantages of the prior art. For example, the inventors envision that aspects of the present invention may provide an industry standard for sample storage, mounting, analysis, and otherwise handling samples, including providing standard calibration samples for samples in all phases (solid, liquid and gas).

As shown in FIG. 15, according to aspects of the invention, sample mounting arrangement 400 includes a sample holder 402 and a sample holder mount 404. A typical sample pellet 406 is also shown in FIG. 15. FIGS. 16, 17, an 18 are a front view, a top plan view, and a side elevation view, respectively, of the sample holder 402 shown in FIG. 15. Sample holder arrangement 400 may be used to position a sample 406 whereby sample 406 can be illuminated by any desired form of radiation, including THz radiation. For example, sample holder arrangement 400 may be used to position a sample 406 in the path of a THz beam produced by apparatus 10 shown in FIGS. 1 and 2.

Sample holder mount 404 may be any structure adapted to receive and retain sample holder 402, for example, another sample holder mount is shown and discussed with respect to FIG. 20 below. In one aspect of the invention, sample holder 402 may be inserted to modular optical device 70 shown in FIGS. 8A and 8B, for example, inserted into slots 74 of device 70.

As shown in FIG. 15, sample holder mount 404 may typically include a base 408 having mounting holes 409, a stanchion 410, for example, a stanchion 410 having supporting gussets 412, and a cavity or recess 414 adapted to receive sample holder 402. For example, stanchion 410 may include recesses or projections adapted to receive corresponding recesses or projections on sample holder 402. In the aspect shown in FIG. 15, stanchion 410 includes a pair of opposing elongated recesses or slots 416 adapted to receive ribs or rails on sample holder 402, though other engagement structures may also be provided. In one aspect, stanchion 410 and sample holder 402 may include interlocking structures, for example, flexile interlocking structures to enhance engagement between stanchion 410 and sample holder 402. For example, FIG. 19 shows a sample holder engagement arrangement 450 according to an alternate aspect of the invention, for instance, that may be incorporated into stanchion 410. As shown in FIG. 19, mounting arrangement 450 having a body 451 with cavity or recess 452 adapted to receive sample holder 402. Body 452 includes slots 453 and a flexible cantilever structure 454. Cantilever structure 454 includes a projection 456 adapted to engage recesses 432 (FIG. 16) in sample holder 402. The projection 456 and cantilever structure 454 may be deflected during insertion of sample holder 402 into recess 452, and deflected manually to remove sample holder 402 from recess 452. Other engagement arrangements will be apparent to those of skill in the art.

As shown in FIGS. 16, 17, and 18, in one aspect, sample holder 402 typically includes a housing or body 420 having a cavity 422 adapted to receive a pellet or fluid-containing (that is, gas or liquid-containing) cell 424 (shown in phantom). Housing 420 includes substantially closed ends 421, a substantially closed bottom 423, an open top 428 for receiving the sample 424 (shown in phantom) into an internal cavity 422, and opposing sides 425 having apertures 426 therein into the internal cavity 422; and means for occluding the open top 428. Housing or body 420 typically includes at least one aperture 426, but typically two opposing apertures 426 adapted to expose cavity 422 (and pellet 424), and an opening 428 for inserting pellet 424. As discussed above, sample holder 402 may typically include structures, for example, projections or recesses, adapted to engage stanchion 410 (See FIG. 15) or another mounting arrangement. In the aspect of the invention shown in FIG. 16-18, sample holder 402 includes a pair of opposing projections or rails 430 adapted to engage recesses or slots 416 in stanchion 410. As shown in FIG. 16, sample holder 402 may also include at least one recess or depression 432 adapted to receive projection 456 on cantilever structure 454 (see FIG. 19).

The open top 428 of sample holder 402 may be sealed or otherwise occluded by various means. For example, open top 428 may be sealed with a cover, for example, the cover or cap 434 shown in FIG. 21. However, in other aspects of the invention open top 428 may be effectively sealed with a hardenable or curable fluid, for example, an epoxy, a silicone, a putty, and a wax, among other hardenable or curable materials and compounds.

Sample holder 402 may also include a handle, flange, or projection 436 to facilitate handling of sample holder 402, for example, manually by a technician or automatedly by, for example, a robotic manipulator. Flange 436 may include a ridge or projection 438 adapted to further facilitate handling. A hole or perforation 440 may also be provided in flange 436, for example, to facilitate handling or storage. In addition, sample holder 402 may also include human or computer readable indicia 442, for example, the nominal size of the sample that can be held by sample holder 442, a manufacturer's name or logo, or related information.

In one aspect of the invention, the one or more apertures 426 may be covered by a radiation transparent barrier, cover or window, for example, a fluid-tight barrier or window transparent to THz radiation, among other forms of radiation. The one or more windows may provide a completely sealed cavity assembly for retaining, among other things, fluids, such as, gases or liquids. In one aspect, when a liquid or gas sample is being handled in an enclosed sample holder 402, sample holder 402 may include one or more fluid inlets or outlets to cavity 422 to introduce or remove a fluid from cavity 422 during, before, or after exposing the fluid sample to radiation.

According to aspects of the invention, sample holder 402 may accommodate pellets or cells 424 ranging from about 0.125 inches to about 3 inches in diameter, but typically is sized to receive pellets or cells 424 with a diameter of about 0.5 inches (12.5 mm). Sample holder 402 may accommodate pellets or cells 424 ranging from about 0.05 mm to about 10 mm in thickness, but typically is sized to receive pellets or cells with a thickness of about 0.1 mm to about 3 mm. In one aspect, a series of sample holders 402 may be provided having varying sizes and thicknesses, for example, a series of holders 402 adapted to accommodate pellets having varying diameters in increments of 0.5 mm.

Sample holder 402 and sample holder mount 404 may be made from any one or more of the metallic or non-metallic materials referenced above. In addition, sample holder 402 and sample holder mount 404 may be fabricated by any one or more of the fabrication methods referenced above. However, in one aspect, sample holder 402 and sample holder mount 404 lend themselves well to fabrication by stereolithograhic methods, as discussed above.

FIG. 20 is a perspective view of another sample holder mount 500 according to another aspect of the invention. As shown, sample holder mount 500 comprises a circler disk 502 having a plurality of recess or cavities 504 adapted to receive a sample holder, for example, sample holder 402 shown in FIGS. 15-18, among others. Cavities 504 may include recesses or projections adapted to receive or engage a sample holder, for example, slots 506 shown in FIG. 20. In one aspect, recesses 504 may be similar to recesses 452 of holder shown in FIG. 19, and include cantilever structures 454 and projections 456.

Sample holder mount 500 typically includes a plurality of mounting holes 508, for mounting holder mount 500 as desired. Sample holder mount 500 with a plurality of sample holders may be oriented horizontally, as shown in FIG. 20, vertically, or at any desired angle. Typically, sample holder mount 500 may be mounted for rotation, for example, manual or automated rotation, to sequentially expose the individual samples positioned in cavities 504 to the desired beam of electromagnetic radiation, for example, THz radiation. In one aspect, sample holder mount 500 may be mounted for rotation before the radiation beam generated by apparatus 10 shown in FIGS. 1 and 2.

According to aspects of the invention, sample holder 402 provides the following benefits.
1. Protection of the pellet or cell 424: By enclosing a fragile pellet 424, placing the pellet into and taking the sample out of a spectrometer, such as, a THz spectrometer, may extend the sample life, for example, by avoiding damage from mishandling or accidents. In addition, assigning a single sample holder to a single sample pellet or cell will minimize the potential of cross-contamination between pellets and or cells.
2. Tagging the pellet or cell 424: Sample holder 402 may include a label which can effectively tag or identity each sample, for example, to avoid the typical need to store each pellet in separate labeled bags or containers.
3. Convenience: Each sample holder 402 easily engages (for example, "snaps into and out of") sample holder mount 404 or 500 (or module 70). Sample mounts may have a variety of forms for different applications. However, as long the sample holder 402 conforms to the same mount engagement, technicians may conveniently engage each different mounting.

As is known in the art, electromagnetic radiation emitters, for example, THz emitters, generally consist of metallic electrode patterns fabricated onto a fast semiconductor substrate such as GaAs, LT GaAs, and silicon on sapphire (SOS). However, few methods and arrangements for mounting these emitters, for example, into a THz system, which are simple to install and do not interfere with optical alignment when replaced or removed are available in this field. Aspects of the present invention address this deficiency.

FIG. 22 is a perspective view of radiation source mounting arrangement 600 according to another aspect of the invention. FIG. 23 is an exploded perspective view of mounting arrangement 600 shown in FIG. 22. As shown in FIGS. 22 and 23, mounting arrangement 600 includes a mounting plate 602 having an aperture 604 positioned to pass an electromagnetic-source-activating laser beam 606, at least one ground contact 608, 609 and a plurality of energizable contacts 610, 611; and a base plate 612 removably mounted to the mounting plate 602. The base plate 612 includes an aperture 614 also positioned to pass the source-activating laser beam 606 and a plurality of electrical contacts 616 adapted to contact the at least one ground contact 608, 609 and at least one of the plurality of energizable contacts 610, 611 on mounting plate 602 to energize an electromagnetic source 618, for example, a THz source, mounted to base plate 612. In one aspect, source mounting arrangement 600 may include one or more heat sinks (not shown), for example, a conventional heat sink positioned to draw heat from source 618.

According to aspects of the invention, the removably mounted base plate 612 is removably mountable (for example, "swappable") to the mounting plate 602 in a plurality of orientations relative to the mounting plate 602 wherein the source 618 may assume a plurality of orientations. Source 618 may be any conventional electromagnetic radiation source that can be activated by a laser beam 606. In one aspect, source 618 may be a THz source, for example, a photoconductive antenna, an E/O crystal, or a surface emitter, among others.

Typically, source 618 is mounted to base plate 602 to best expose the source 618 to laser beam 606. For example, source 618 may be mounted on the near side of base plate 602, illuminated by laser beam 606 and the generated radiation is emitted in the general direction indicated by arrow 607. However, in another aspect, source 618 may be positioned on the far side of base plate 602 and illuminated by a laser beam in a direction opposite arrow 607 to emit radiation in the general direction opposite to the direction of arrow 606.

According to aspects of the present invention, base plate 612 may be easily separated from mounting plate 602, for example, by using a flat screwdriver, tweezers, or by hand. Base plate 612 may be provided as a disposable medium, for example, a disposable medium for THz emitters. For example, once the source 618 burns out or otherwise fails, it can be disposed of and replaced with a new one. Accordingly, aspects of the invention may reduce the down time of current systems, for example, current THz systems.

Figure 26:
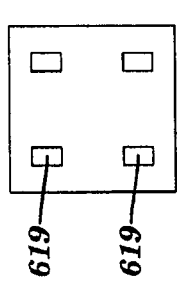
FIG. 26 is a rear plan view of a typical radiation source that may be used in the aspect of the invention shown in FIGS. 22 and 23.
Figure 25:
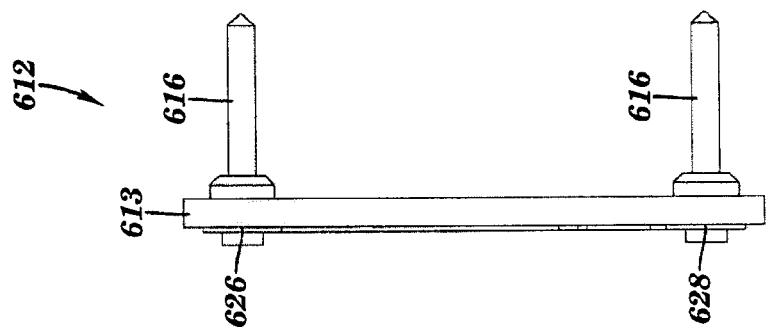
FIGS. 24 and 25 are a top plan and a side elevation view, respectively, of the base plate shown in FIGS. 20 and 21.
Figure 24:
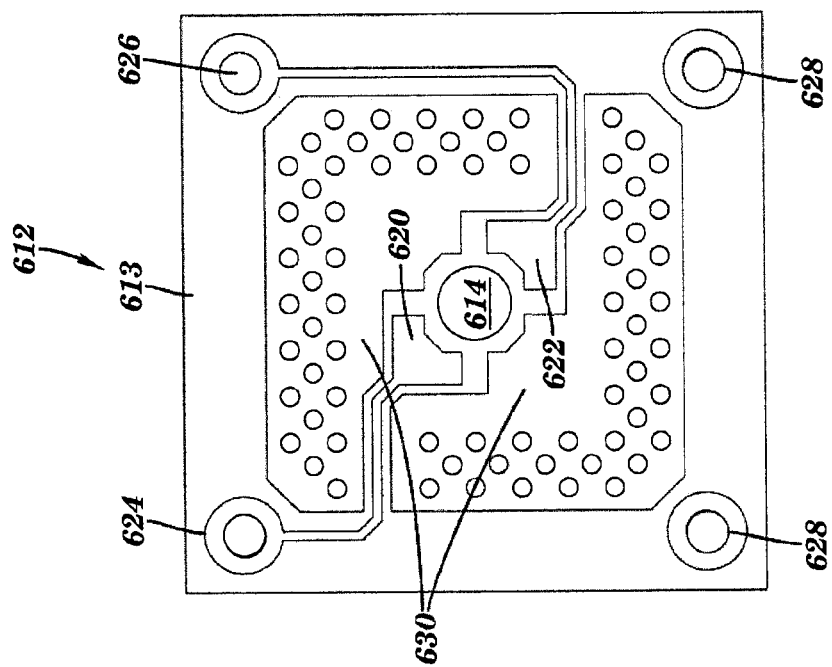

FIGS. 24 and 25 are a top plan view and a side elevation view, respectively, of the base plate 612 shown in FIGS. 22 and 23. FIG. 26 is a rear plan view of a typical source 618. FIGS. 27 and 28 are a top plan view and a side elevation view, respectively, of the base plate 612 shown in FIGS. 22 and 23. As shown in FIGS. 24 and 25, base plate 612 comprises a substantially flat plate 613, typically, a non-conductive plate, having isolated planar electrodes 620 and 622 mounted thereon. Typically, electrodes 620 and 622 comprise conductive material, for example, copper, positioned to contact electrodes on source 618, for example, electrodes 619 of source 618 shown in FIG. 26. Source 618 may be mounted to base plate 612 in a conventional manner, for example, using silver paste. According to aspects of the invention, electrode 620 is electrically coupled to contact 624 and electrode 622 is electrically coupled to contact 626. Base plate 612 may also include one or more planar heat sinks 630 adapted to draw heat form source 618 when mounted on base plate 612. Contacts 624 and 626 are electrically coupled to contacts 616 on the opposite side of plate 613. Contacts 616 are positioned and adapted to electrically couple with contacts 608, 609, 610, and 611, respectively, on base plate 602. As shown in FIG. 25, in one aspect, contacts 616 may comprise pins adapted to be received by sleeves in mounting plate 602.

As shown in FIGS. 27 and 28, mounting plate 602 comprises a substantially flat plate 603, again, typically, a non-conductive plate, having a through hole 632, a plurality of electrical contacts 608, 609, 610, 611 and a plurality of mounting holes 634 for mounting mounting plate 602. Mounting holes 634 may typically be 4-40 thru screw holes for easy mounting from one side. Typically, contacts 608, 609, 610, and 611 comprise conductive material, for example, copper, and are positioned to contact electrodes on base plate 612. Contacts 608, 609, 610, and 611 are electrically coupled to contacts 636, 637, 638, and 639, respectively, on the opposite side of plate 63. In one aspect, contacts 608 and 611 on mounting plate 602 are connected to the signal used to drive the source 618 and contacts 609 and 610 are connected to ground. In one aspect, the likelihood of a signal shorting to ground is minimal if non-existent. As shown contacts 636, 637, 638, and 639 may comprise pins, for example, pins adapted to be inserted into an SMA mount. In one aspect, of the invention, contacts 608 and 610 are adapted to receive pin contacts 616 on base plate 602. Contacts 608 and 610 may comprise, holes, slots, or sleeves adapted to receive and electrically contact pin contacts 616.

According to aspects of the invention, base plate 602 having source 618 may be replaceably mounted to mounting plate 602 to replace, service, or re-orient base plate 602 and source 618. For example, contact pins 616 of base plate may be replaceably inserted into contact sleeves 608 and 610 to replace, service, or re-orient base plate 602 and source 618. In the aspect of the invention shown in FIGS. 22-28, base plate 612 may be engaged with mounting plate 602 in four (4) orientations, equally spaced 90 degrees from each other. As a result, the aspect shown in FIGS. 22-28 provides four different orientations for source 618 by simply engaging and disengaging pins in base plate 612 with sleeves in mounting plate 602. For example, when source 618 is a THz source, aspects of the invention enable the technician to switch the generated THz polarization and polarity by simply re-orienting base plate 612.

FIG. 29 is a schematic view of another radiation source mounting arrangement 650 according to another aspect of the invention. In another aspect, the arrangement 650 provides for an larger number of electrical contacts between a mounting plate and a base plate while keeping the ability to easily re-orient, exchange or swap out a source, for example, a THz emitter. In the aspect of the invention shown in FIG. 29, a single source may be mounted for rotation so that the user can rotate the base and source to vary a source orientation, and polarization, through 360 degrees.

Arrangement 650 includes a mounting plate 652 having an aperture (not shown) positioned to pass an electromagnetic-source-activating laser beam (not shown), at least one ground contact 654 and a plurality of energizable contacts 656; and a base plate 658 removably mounted and/or rotatably mounted to mounting plate 652. The base plate 658 includes an aperture 664 (shown in phantom) also positioned to pass the source-activating laser beam and a plurality of electrical contacts 660 adapted to contact at least one ground contact 654 and at least one of the plurality of energizable contacts 656 on mounting plate 652 to energize an electromagnetic source 668, for example, a THz source, mounted to base plate 652. In one aspect, source mounting arrangement 650 may include one or more heat sinks (not shown), for example, a conventional heat sink positioned to draw heat from source 668.

FIGS. 30A and 30B are a top plan view and a side elevation view, respectively, of another radiation source mounting arrangement 700 according to another aspect of the invention. Arrangement 700 is similar in design and operation to that of a conventional digital camera memory card. Arrangement 700 includes a base plate 702 having a radiation source 704 and multiple electrical contacts 706 for interfacing with a mounting (not shown). The mounting provides contacts connected to a signal used to drive the source 704 and contacts connected to ground. The source 704, for example, a THz emitter chip, is mounted (electrode pattern into the page of FIG. 30A) onto base plate 702.

According to aspects of the invention, base plate 702 may easily be inserted into a mounting, for example, a slotted mounting, via flanges 708 on either side of base plate 702. When base plate 702 is fully inserted, the electrical contacts 706 make contact with appropriate connectors. By having the option of numerous electrical connections, the source 704 may include more than a single emitter, for example, multiple THz emitters. Each source emitter included in source 704 may include 1-dimensional arrays of linear electrodes (that is, metallic lines). Each linear electrode may contact a separate connection in the mount. Accordingly, the user may specify which electrode is connected to ground and which electrode is connected to the signal. The electrodes on the source 704 may be spaced at equal or different distances. In aspects of the invention, a source 704 may include multiple emitters of a single gap width or multiple emitters of a variety of gap widths, for example, multiple THz emitters.

According to aspects of the invention, the interconnect system between the mounting (again, not shown) and arrangement 700 may be much like that of current digital camera memory cards, for example, with contact on one or two edges. The arrangement 700 according to aspects of the invention is very convenient for exchanging or swapping emitters in and out. However, emitters with an even larger number of electrodes would not need to be replaced as often as single emitter sources. In some aspects, the "quad flat pack standard" (used for surface mount ICs) may be used and the mounting may include a zero-insertion force socket (ZIF). Other suitable mounting arrangements will be apparent to those of skill in the art.

According to another aspect of the invention, the orientation of a source of radiation, for example, a THz source, may be provided by using multiple contacts and a multi-electrode emitter in which the biasing electric field may be rotated without physically rotating the base.

Figure 31:
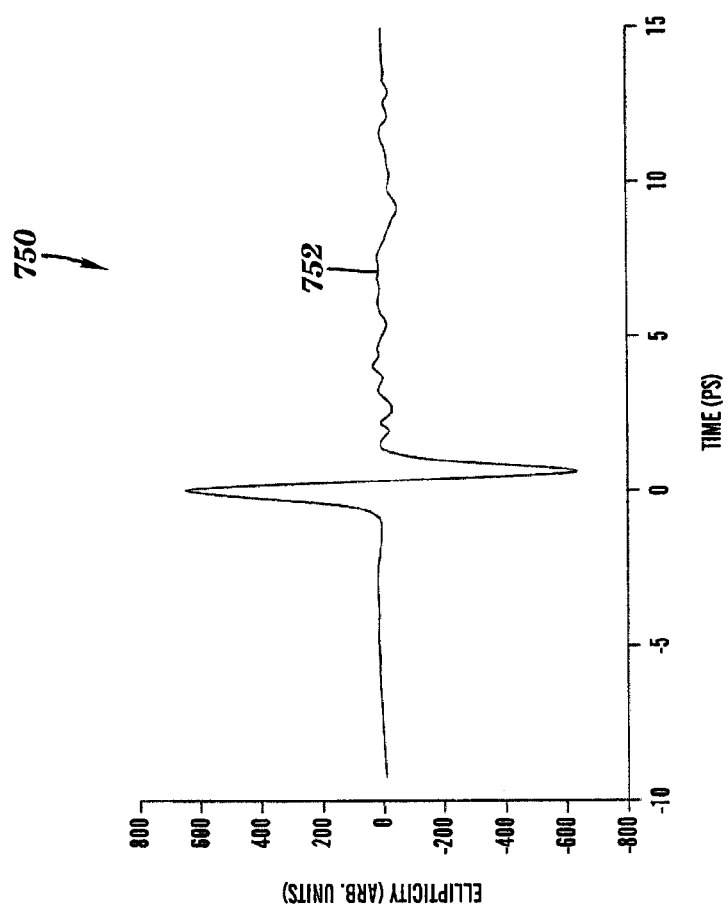
FIG. 31 is a typical baseline time-domain graph of the polarization ellipticity modulation detected according to one aspect of the invention.

FIGS. 31-35 provide typical examples of the output that can be obtained employing aspects of the present invention. FIG. 31 is a typical baseline time-domain graph of the polarization ellipticity modulation detected according to one aspect of the invention when no sample is present. For example, the curve 752 shown in FIG. 31 was obtained by the apparatuses shown in FIGS. 9-13 employing a THz source and detector and with the "auto-balance" mechanism shown in FIGS. 12 and 13. Curve 752 represents the radiation field detected by measuring the polarization ellipticity of the modulated probe signal without passing the THz through a sample. The abscissa of curve 752 is time in picoseconds (ps), and is normalized about the THz pulse shown. The ordinate of curve 752 is in arbitrary units of "polarization ellipticity."

Figure 32:
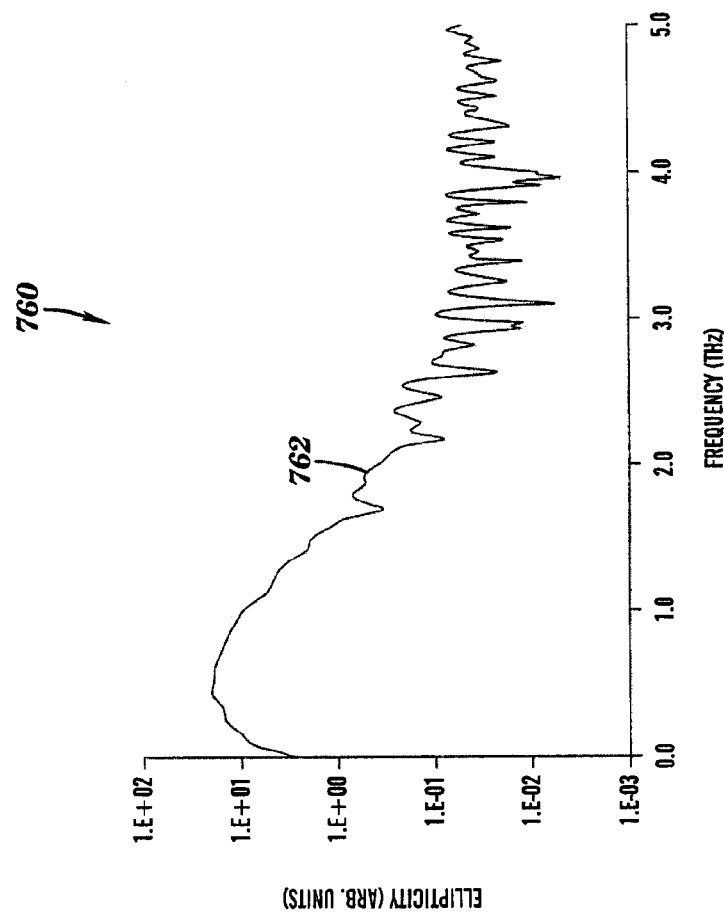
FIG. 32 is a typical baseline frequency-domain graph of the time-domain polarization ellipticity modulation shown in FIG. 31.

FIG. 32 is a typical baseline frequency-domain graph 760 of the time-domain polarization ellipticity modulation shown in FIG. 31.

Figure 33:
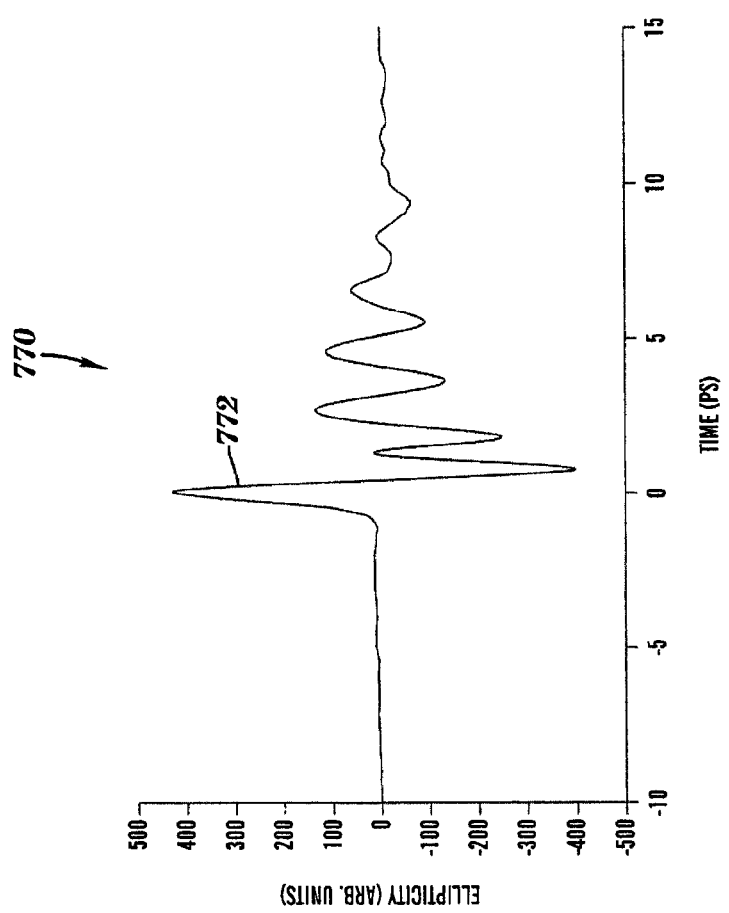
FIG. 33 is a typical time-domain graph of the polarization ellipticity modulation detected for a sample according to one aspect of the invention.
Figure 34:
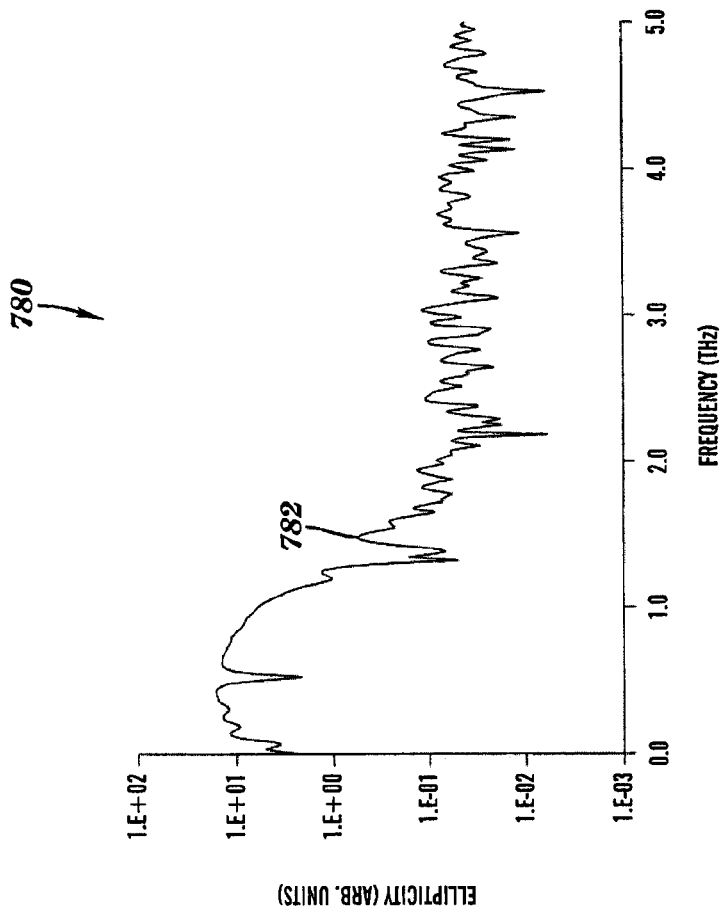
FIG. 34 is a frequency-domain graph of the time-domain polarization ellipticity modulation shown in FIG. 33.

FIG. 33 is a typical time-domain graph 770, similar to FIG. 31, of the polarization ellipticity modulation detected for a sample according to one aspect of the invention. The data shown in FIG. 33 was obtained in a similar fashion as the data sown in FIG. 31, but for the data shown in FIG. 33 a THz beam was reflected off a sample of alpha-lactose, for example, using the modular optic 70 shown in FIGS. 8A and 8B. Other samples generate similar curves. FIG. 34 is a typical frequency-domain graph 780 of the time-domain polarization ellipticity modulation shown in FIG. 33.

Figure 35:
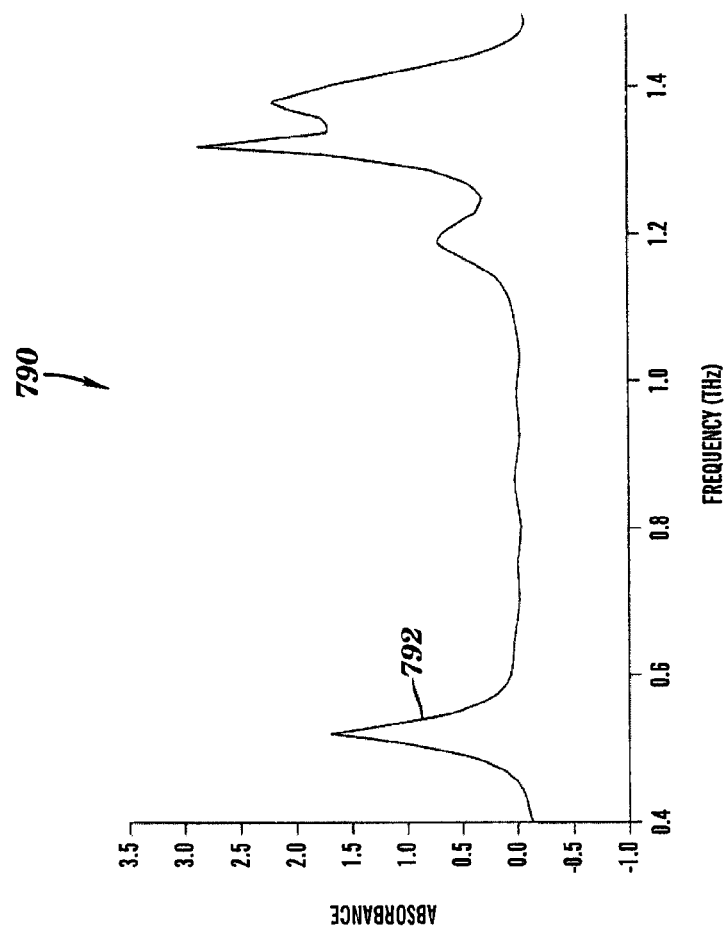
FIG. 35 is a typical frequency-domain comparison of the probe beam modulation of the ellipticities shown in FIGS. 32 and 34.

FIG. 35 is a typical frequency-domain comparison 790 of the probe beam modulation of the ellipticities shown in FIGS. 32 and 34. In FIG. 35, the peaks in curve 792 represents the absorbance of the alpha-lactose sample of THz radiation at frequency compared the base-line test in which no sample was present.

Methods, apparatus, and devices have been presented for manipulating and characterizing electromagnetic fields, in particular, THz fields, that heretofore were difficult or impossible. Any form of electromagnetic field that can be manipulated and characterized may be used for the multiple aspects disclosed. In the THz field, aspects of the invention provide methods and apparatus for detecting and characterizing a broad range of materials, from explosives and explosive related compounds to pharmaceuticals. However, the materials for which aspects of the invention may be employed are unlimited. The inventors envision that with the advancement in the technology represented by aspects of invention, more materials can be detected and analyzed using THz technology.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. An electromagnetic radiation source mounting arrangement comprising:
a mounting plate having an aperture positioned to pass a radiation-source-activating pump laser beam, at least one ground contact, and a plurality of energizable contacts;
and a base plate mounted to the mounting plate, the base plate having an aperture positioned to pass the radiation-source-activating pump laser beam and a plurality of electrical contacts adapted to contact the at least one ground contact and at least one of the plurality of energizable contacts on the mounting plate to energize a radiation source mounted to the base plate.

2. The radiation source mounting arrangement as recited in claim 1, wherein the base plate is mountable to the mounting plate in a plurality of orientations relative to the mounting plate wherein the radiation source assumes a plurality of orientations.

3. The radiation source mounting arrangement as recited in claim 2, wherein the plurality of orientations comprise at least 4 orientations.

4. The radiation source mounting arrangement as recited in claim 2, wherein the base plate is a circular base plate having a plurality of contacts.

5. The radiation source mounting arrangement as recited in claim 4, wherein the plurality of contacts comprise more than 4 contacts.

6. The radiation source mounting arrangement as recited in claim 4, wherein the circular base plate is rotatably mounted to the mounting plate.

7. The radiation source mounting arrangement as recited in claim 6, wherein the rotatably-mounted, circular base plate is adapted to rotatably vary the orientation of the source mounted to the base plate.

8. The radiation source mounting arrangement as recited in claim 6, wherein the at lease one ground contact on the rotatably-mounted, circular base plate comprises a plurality of ground contacts distributed about a periphery of the rotatably-mounted, circular base plate.

9. The radiation source mounting arrangement as recited in claim 1, wherein the plurality of energizable contacts in the mounting plate comprises a plurality of sleeves and the plurality of electrical contacts on the base plate comprise a plurality of pins engagable with the plurality of sleeves.

10. The radiation source mounting arrangement as recited in claim 1, wherein the source comprises a terahertz source.

11. The radiation source mounting arrangement as recited in claim 10, wherein the terahertz source comprises a terahertz antenna.

12. The radiation source mounting arrangement as recited in claim 1, wherein the base plate is removably-mounted to the mounting plate.

13. A method of mounting a terahertz source comprising:
providing a mounting plate having an aperture positioned to pass a terahertz source-activating pump laser beam, at least one ground contact, and a plurality of energizable contacts;
providing a base plate having an aperture positioned to pass the terahertz source-activating pump laser beam and a plurality of electrical contacts to energize a terahertz source mounted to the base plate; and
mounting the base plate to the mounting plate wherein the electrical contacts on the base plate contact the at least one ground contact and at least one of the plurality of energizable contacts on the mounting plate.

14. The method as recited in claim 13, wherein mounting the base plate to the mounting plate comprises mounting the base plate to the mounting plate wherein the base plate and the terahertz source are mounted in a first orientation relative to the mounting plate, and wherein the method further comprises:
removing the base plate from the mounting plate; and
remounting the base plate to the mounting plate wherein the base plate and the terahertz source are mounted in a second orientation, different from the first orientation, relative to the mounting plate.

15. The method as recited in claim 13, wherein the plurality of energizable contacts in the mounting plate comprises a plurality of sleeves and the plurality of electrical contacts on the base plate comprise a plurality of pins, and wherein mounting the base plate to the mounting plate comprises engaging the plurality of pins with the plurality of sleeves.

16. The method as recited in claim 13, wherein the terahertz source comprises a terahertz antenna.

* * * * *